US011045500B2

(12) United States Patent
Levenberg et al.

(10) Patent No.: US 11,045,500 B2
(45) Date of Patent: Jun. 29, 2021

(54) TISSUE ENGINEERING CONSTRUCT COMPRISING FIBRIN

(75) Inventors: Shulamit Levenberg, Moreshet (IL); Ayelet Lesman, Haifa (IL)

(73) Assignee: TECHNION RESEARCH DEVELOPMENT FOUNDATION LTD., Haifa (IL)

( * ) Notice: Subject to any disclaimer, the term of this patent is extended or adjusted under 35 U.S.C. 154(b) by 934 days.

(21) Appl. No.: 13/985,388

(22) PCT Filed: Feb. 13, 2012

(86) PCT No.: PCT/IL2012/000074
§ 371 (c)(1),
(2), (4) Date: Oct. 30, 2013

(87) PCT Pub. No.: WO2012/111000
PCT Pub. Date: Aug. 23, 2012

(65) Prior Publication Data
US 2014/0050766 A1    Feb. 20, 2014

Related U.S. Application Data

(60) Provisional application No. 61/442,570, filed on Feb. 14, 2011.

(51) Int. Cl.
| A61K 35/33 | (2015.01) |
| A61L 27/38 | (2006.01) |
| A61L 27/22 | (2006.01) |
| A61L 27/48 | (2006.01) |
| A61L 27/50 | (2006.01) |
| A61K 9/14  | (2006.01) |

(52) U.S. Cl.
CPC .............. *A61K 35/33* (2013.01); *A61K 9/148* (2013.01); *A61L 27/225* (2013.01); *A61L 27/3808* (2013.01); *A61L 27/3886* (2013.01); *A61L 27/48* (2013.01); *A61L 27/507* (2013.01)

(58) Field of Classification Search
None
See application file for complete search history.

(56) References Cited

U.S. PATENT DOCUMENTS

| 6,110,459 A * | 8/2000 | Mickle ............. A61K 35/34 424/85.1 |
| 2004/0009589 A1* | 1/2004 | Levenberg .......... C12N 5/069 435/366 |
| 2004/0115176 A1* | 6/2004 | Swartz .............. A61L 27/225 424/93.7 |
| 2005/0276864 A1* | 12/2005 | LeTort ............... C12N 5/0657 424/548 |
| 2006/0018838 A1* | 1/2006 | George ............... A61L 27/3808 424/44 |
| 2006/0153815 A1 | 7/2006 | Seyda et al. |
| 2006/0198827 A1* | 9/2006 | Levenberg .......... C12N 5/0657 424/93.7 |
| 2009/0169521 A1 | 7/2009 | Levenberg et al. |

FOREIGN PATENT DOCUMENTS

| DE | 10313284 A1 | 10/2004 |
| WO | 2004038004 A2 | 5/2004 |
| WO | 2004084968 A1 | 10/2004 |
| WO | 2006084040 A2 | 10/2006 |
| WO | 2007035712 A2 | 3/2007 |
| WO | 2008008229 A2 | 1/2008 |

OTHER PUBLICATIONS

Kunz-Schughart LA et al. 2006. Potential of fibroblasts to regulate the formation of three-dimensional vessel-like structures from endothelial cells in vitro. Am J Physiol Cell Physiol 290: C1385-98.*
Ghajar et al. (The Effect of Matrix Density on the Regulation of 3-D Morphogenesis. Biophysical Journal, 2008 94:1930-1941).*
Levenberg et al. (Engineering vascularized skeletal muscle tissue. Nature Biotechnology (2005) 23(7):879-88).*
Huang et al. (Rapid formation of functional muscle in vitro using fibrin gels. J. Appl Physiol 98: 706-713, 2005).*
Nahm et al. (Sustained ability for fibroblast outgrowth from stored neonatal foreskin: a model for studying mechanism of fibroblast outgrowth, Journal of Dermatological Science. 2000, 28(2): 152-158).*
Zund et al. (Tissue engineering: A new approach in cardiovascular surgery; Seeding of human fibroblasts followed by human endothelial cells on resorbable mesh. European Journal of Cardio-thoracic Surgery 13 (1998) 160-164).*
Sukmana et al. Biomaterials (2010) 31: 5091-5099 (Year: 2010).*
Narayan et al. J. Biomed. Mater Res (2008) 87A: 710-718). (Year: 2008).*
Ahmed et al; "Fibrin: a versatile scaffold for tissue engineering applications" Tissue engineering. Part B, Reviews 14(2):pp. 199-215.(2008).
Beier et al:"De novo generation of axially vascularized tissue in a large animal model". Microsurgery. 29: pp. 42-51. (2009).
Caspi et al:. "Tissue engineering of vascularized cardiac muscle from human embryonic stem cells". Circ Res. 100(2): pp. 263-272. (2007).
Chen et al; "Prevascularization of a Fibrin-Based Tissue Construct Accelerates the Formation of Functional Anastomosis with Host Vasculature". Tissue Eng part A. 15(6):pp. 1363-1371.(2009).

(Continued)

*Primary Examiner* — Susan M Hanley
(74) *Attorney, Agent, or Firm* — Browdy and Neimark, PLLC

(57) ABSTRACT

A three-dimensional fibrin engineered tissue construct is provided selected from: (i) a fibrin gel matrix comprising a combination of tissue-specific cells and at least one type of vascular cells; and (ii) a hybrid scaffold of fibrin gel and a polymeric synthetic scaffold comprising at least one type of vascular cells or a combination of tissue-specific cells and at least one type of vascular cells.

22 Claims, 20 Drawing Sheets

(56) References Cited

OTHER PUBLICATIONS

Duong et al: "Modulation of 3D Fibrin Matrix Stiffness by Intrinsic Fibrinogen—Thrombin Compositions and by Extrinsic Cellular Activity" Tissue Engineering: Part A vol. 15, pp. 1865-1876. (2009).
Geer et al; "Fibrin-mediated delivery of KGF in 2D and 3D models of wound regeneration" Engineering in Medicine and Biology, 2002. 24th Annual Conference and the Annual Fall Meeting of the Biomedical Engineering Society EMBS/ BMES Conference, (2002).
Gundy et al; "Human coronary artery smooth muscle cell response to a novel PLA textile/fibrin gel composite scaffold" Acta Biomater 4(6):pp. 1734-1744. (2008).
Kaully et al : "Vascularization—The Conduit to Viable Engineered Tissues" Tissue Engineering: Part B vol. 15, pp. 159-168.(2009).
Langer et al: "Tissue Engineering" Scinese, vol. 260, pp. 920-926. (1993).
Lesman et al; "Transplantation of a tissue-engineered human vascularized cardiac muscle". Tissue Eng Part A. 16 (1):115-25 (2010).
Lesman et al; "Engineering vessel-like networks within multicellular fibrin-based constructs" Biological Engineering Society 32(31) pp. 7856-7869. (2011).
Levenberg et al; Differentiation of human embryonic stem cells on three-dimensional polymer scaffolds. PNAS USA 100(22):pp. 12741-12746.(2003).
Levenberg et al;Engineering vascularized skeletal muscle tissue. Nat Biotechnol. 23(7):pp. 879-884. (2005).
Levenberg S ; "Co-Culture Systems for Tissue Regeneration". European Cells and Materials 16 Suppl. 3 p. 26. (2008).
Montano et al;Formation of Human Capillaries In Vitro: The Engineering of Prevascularized Matrices. Tissue Eng part A. 16(1): pp. 269-282.(2010).
Mooney et al;. "Long-term engraftment of hepatocytes transplanted on biodegradable polymer sponges". J Biomed Mater Res. 37(3):pp. 413-420. (1997).
Munirah et al;"Fibrin and poly(lactic-co-glycolic acid) hybrid scaffold promotes early chondrogenesis of articular chondrocytes: an in vitro study" Journal of Orthopaedic Surgery and Research pp. 1-10. (2008).
Munirah et al; The use of fibrin and poly(lactic-co-glycolic acid) hybrid scaffold for articular cartilage tissue engineering: an in vivo Analysis. European cells and matetials 15:pp. 41-52. (2008).
Smith et al; "Improved growth factor directed vascularization into fibrin constructs through inclusion of additional extracellular molecules" Microvascular Research 73 pp. 84-94. (2007).
Trkov et al; "Micropatterned 3-Dimensional Hydrogel System to Study Human Endothelial-Mesenchymal Stem Cell Interactions" J Tissue Eng Regen Med. 4(3): pp. 205-215.(2010).
Vailhe et al; In vitro angiogenesis is modulated by the mechanical properties of fibrin gels and is related to alpha-v/beta-3 integrin localization. In vitro Cell. Dev. Biol.—Animal 33:pp. 763-773. (1997).
Van Hinsbergh et al; "Role of Fibrin Matrix in Angiogenesis" Annals of the New York Academy of Sciences 936, pp. 426-437. (2001).
Willerth et al; "Optimization of Fibrin Scaffolds for Differentiation of Murine Embryonic Stem Cells into Neural Lineage Cells" Biomaterials.December ; 27(36): pp. 5990-6003. (2006).
International Search Report and Written Opinion from International Appln. No. PCT/IL2012/000074 dated Jul. 10, 2012.
Ghajar, et al., Mesenchymal Stem Cells Enhance Angiogenesis in Mechanically Viable Prevascularized Tissues via Early Matrix Metalloproteinase Upregulation, Tissue Engineering, 2006, pp. 2875-2888, vol. 12, No. 10.
Heiss, et al., Endothelial cell spheroids as a versatile tool to study angiogenesis in vitro, The FASEB Journal, Research Communication, 2015, pp. 3076-3084, vol. 29(7).
Kleinman and Martin, "Matrigel: Basement membrane matrix with biological activity," Seminars in Cancer Biology 15:378-386 (2005).
Wikipedia entry for Matrigel(TM), downloaded Mar. 14, 2018 from en.wikipedia.org/wiki/Matrigel.
Swartz et al., Engineering of fibrin-based functional and implantable small-diameter blood vessels, Am J Physiol Heart Circ Physiol, 288:H1451-H1460 (2005).
Pashneh-Tala et al., The Tissue-Engineered Vascular Graft—Past, Present, and Future, Tissue Engineering, Part B , 22(1):68-10 (2016).
Lee et al., Generation of Multi-Scale Vascular Network System within 3D Hydrogel using 3D Bio-Printing Technology, Cell Mol Bioeng. 7(3): 460-472 (2014).

* cited by examiner

X4 x10

Fibrin   PLLA/PLGA

Fig. 6A       Fig. 6B       Fig. 6C
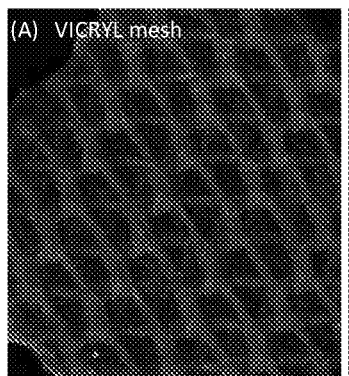 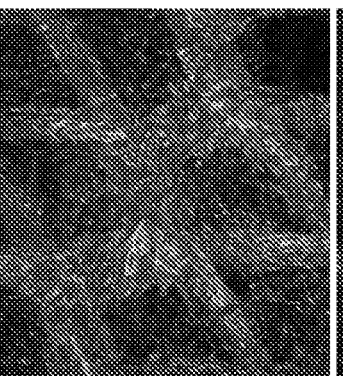 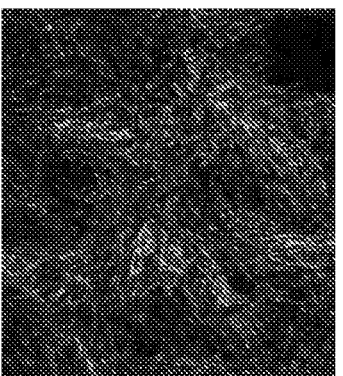
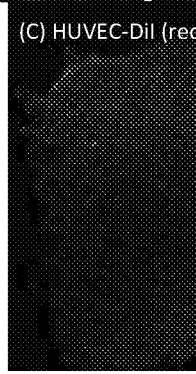
Fig. 6D       Fig. 6E

TISSUE ENGINEERING CONSTRUCT COMPRISING FIBRIN

RELATED APPLICATIONS

This application is a national phase filing under 35 U.S.C. 371 of PCT International Application No. PCT/IL2012/000074, filed on Feb. 13, 2012, which claims the benefit of U.S. Provisional Application No. 61/442,570 filed on Feb. 14, 2011, the entirety of these applications is hereby incorporated herein by reference for the teachings therein.

FIELD OF THE INVENTION

The present invention is in the field of tissue engineering and, in particular, it relates to tissue engineering constructs comprising fibrin, capable of generating functional vascular network, and methods of making same.

BACKGROUND OF THE INVENTION

Promotion of vascularization, the process in Which new blood vessels assemble, is critical for a number of pathological conditions and surgical interventions as well as for the construction of viable tissue-engineered constructs. Wound healing, myocardial ischemia, peripheral vascular disease, islet cell transplantation, and plastic reconstruction surgery are a few of many pathological situations that would be improved due to enhanced vascularization. For tissue engineering, vascularization could maintain cell viability during in vitro construct growth, induce tissue organization and differentiation, and promote graft survival upon implantation.

Tissue engineering holds an enormous potential for replacing or restoring the function of damaged tissues. However, the most successful applications have been limited to thin avascular tissues such as skin and cartilage in which delivery of nutrients and oxygen relies on passive diffusion through the construct. After transplantation, the engineered tissue is prone to ischemia and host blood supply is not adequate to allow graft viability, mainly in the first days after transplantation. Therefore, a functional vascular network must be generated to deliver blood quickly upon implantation.

In engineering tissue-constructs for regenerative medicine, self-assembly of vessel networks can be induced within 3D scaffolds in vitro by means of multicellular culturing of endothelial cells (ECs), vascular mural cells and cells specific to the tissue of interest. The vascular mural cells are smooth muscle cells or pericytes, which provide physical support to ECs, generate extra-cellular proteins (like collagen, laminin, fibronectin) and release pro-angiogenic growth factors (such as VEGF, FGF, TGF, Angiopoietin) which induce vascularization. Embryonic fibroblasts and mesenchymal precursor cells are extensively used in tissue multicellular protocols due to their high differentiation capacity toward development into mural cells. The multicellular approach both support formation of endothelial vessels and promotes EC and tissue-specific cell interactions, suggested to play a key role in further tissue-construct development and differentiation. Such endothelial vessels consisting of tube-like openings may form the basis for improved media penetration to the inner regions of thick three-dimensional (3D) constructs, enhancing construct survival and enabling effective engineering of large complex tissues in the lab. Upon implantation, the pre-existed blood vessels can integrate with host vasculature, enhancing graft perfusion and accelerating host neovascularization via paracrine signaling pathways.

In our previous studies (see US 2005/0031598; US 2006/0198827; US 2009/0169521; Levenberg et al., 2005; Caspi et al., 2007; Lesman et al., 2010), we have demonstrated that a vascularized skeletal and cardiac muscle tissue can be generated by seeding a heterogeneous population of cells on a three-dimensional scaffold. Prevascularization of the engineered skeletal and cardiac muscle tissue resulted in enhanced tissue functionality in vitro and promoted perfusion of the graft after transplantation.

One key aspect in tissue engineering is the choice of scaffold biomaterial into which cells are seeded, grow and proliferate establishing the new tissue substitute. Biomaterial properties have been shown to directly effect cell organization and differentiation. Thus, modification of biomaterial composition of scaffolds may provide a powerful approach to explore and optimize vascularization in vitro and in vivo. Choice of scaffold biomaterial must consider both requisites for structural support of cells (typically provided by synthetic scaffolds) and for biological interactions (usually provided by naturally harvested materials) allowing for cell adhesion, migration, and differentiation into functional tissue.

Attempts at preparing prevascularized matrices have been disclosed by Montano et al. (2010) and Chen et al. (2009). Vailhe et al. (1997) report capillary formation in matrices comprising fibrin gel. WO 2008/008229 discloses a tissue module for generating vascularized tissue, particularly bone tissue, comprising a biocompatible matrix, tissue progenitor cells, and vascular progenitor cells.

There is still a need in the art to provide 3D tissue constructs that enhance vascularization in various tissue engineering applications.

SUMMARY OF THE INVENTION

The present invention relates to fibrin-based 3D engineered tissue constructs, to methods for their preparation and to pharmaceutical compositions comprising them.

In some embodiments, the invention relates to a three-dimensional fibrin engineered tissue construct selected from:
(i) a fibrin gel matrix comprising a combination of tissue-specific cells and at least one type of vascular cells; and
(ii) a hybrid scaffold of fibrin gel and a polymeric synthetic scaffold comprising at least one type of vascular cells or a combination of tissue-specific cells and at least one type of vascular cells.

The fibrin gel alone or in combination with a polymeric synthetic scaffold such as (poly-l-lactic acid/polylactic-co-glycolic acid) PLLA/PLGA sponge can serve as a supporting 3D matrix for the formation of various engineered tissues in vitro as well as for the integration of vascular network within the engineered tissue of choice. In some embodiments, the construct comprises at least one type of vascular cells, preferably a co-culture of two types or more of vascular cells for generating a tissue with only blood-vessels. In some other embodiments, the construct comprises a combination of one, two or more types of vascular cells and tissue specific cells for the formation of a three-dimensional engineered tissue comprising internal blood vessel architecture. The cell culture comprising one type of cells or a combination of cell types is also termed hereinafter "cellular preparation".

The invention also relates to a method for the preparation of said three-dimensional fibrin engineered tissue construct, comprising the steps:
  (i) mixing at least one type of vascular cells or a combination of at least one type of vascular cells and tissue specific cells with a thrombin solution and transferring the thrombin-cell suspension to a silicone tube mold that may contain a polymeric synthetic scaffold at the bottom;
  (ii) adding a solution of fibrinogen to the silicone tube mold and mixing for a short, period;
  (iii) incubating the silicone tube mold to allow polymerization of the fibrinogen; and
  (iv) removing the silicone tubes and adding a cell medium, thus obtaining the desired three-dimensional fibrin engineered tissue construct.

The invention further relates to pharmaceutical compositions comprising the three-dimensional fibrin engineered tissue construct of the invention.

BRIEF DESCRIPTION OF THE FIGURES

FIGS. 6A-6E show images of a 3D fibrin-VICRYL™ construct embedded with a co-culture of endothelial and fibroblast cells. (6A) VICRYL™ mesh is observed with its blue autofluorescence intensity. Endothelial cells formed a confluent layer as indicated by staining with VWF antibody (green, 6B and 6C) and by DiI reagent (red, 6D and 6E).

DETAILED DESCRIPTION OF THE INVENTION

Figure 1:
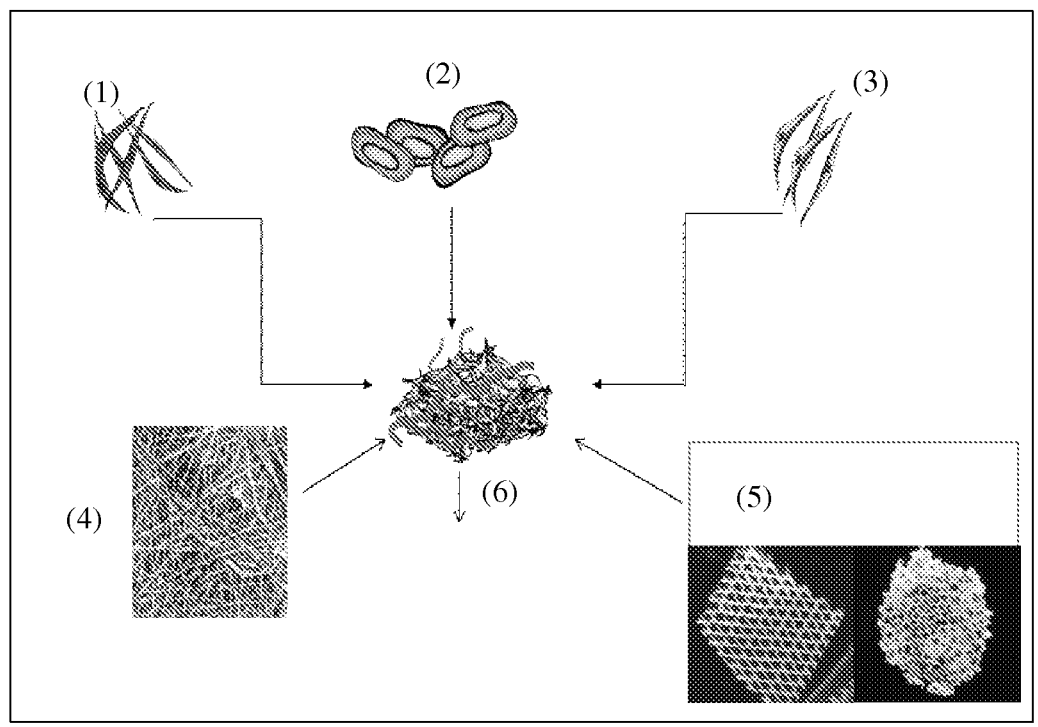
FIG. 1 shows a schematic representation of the components used for the preparation of 3D fibrin-based constructs according to the invention: (1) fibroblasts; (2) human endothelial cells; (3) myoblasts; (4) fibrin; (5) synthetic scaffold (PLLA/PLGA sponge or Vicryl mesh; and (6) tissue substitutes with internal blood network.

Most cell therapy procedures available today focus on direct cell injection to the site of tissue injury or to the blood stream, without any additional biomaterials. However, in such procedures, more than 70% of the injected cells die or are washed away within the first days of injection, posing a critical obstacle to direct injection of cells. Combination of cells with scaffolds designed to generate engineered patches can reduce cell loss and preserve cells in the desired engraftment position in vivo. Even when three-dimensional engineered tissues are constructed based on biomaterials, they usually do not incorporate an integrated blood vessel network. Consequently, the transplanted cells are not able to receive nutrients and oxygen in vivo and the construct cannot survive. Thus, the development of a functional blood vessel network within the engineered tissues is of high importance for both initial survival of the transplanted tissue, as well as for appropriate development of the tissue in vitro.

Fibrin is a natural polymer and can thus provide a good support to the cells. In addition, fibrin is a known blood vessel inducer (angiogenic), as shown by numerous research studies (e.g. Victor et al., 2001).

To date, fibrin matrix has been widely studied in tissue engineering of soft tissues such as cartilage and skin, or used as an injectable carrier material for cell therapy procedures. Also, investigation of angiogenesis/vasculogenesis in systems involving fibrin matrix or synthetic scaffolds have been described, but has never been applied in complex constructs involving fibrin together with synthetic scaffold for culturing multicellular preparations. In such complex cellular preparations, the delicate needs of the different cell types must be considered, especially with regard to their migration, organization and differentiation capabilities.

In one aspect, the present invention relates to a three-dimensional fibrin engineered tissue construct selected from:
  (i) a fibrin gel matrix comprising a combination of tissue-specific cells and at least one type of vascular cells; and
  (ii) a hybrid scaffold of fibrin gel and a polymeric synthetic scaffold comprising at least one type of vascular cells or a combination of tissue-specific cells and at least one type of vascular cells.

In certain embodiments, the fibrin gel is obtained from a mixture of fibrinogen and thrombin. One example of fibrinogen is biological active component 2 or BAC2, which is a sterile solution, pH 6.7-7.2, consisting mainly of a concentrate of human fibrinogen, and further comprises: fibronectin, albumin, plasminogen, Factor XIII, Factor VIII, and von Willebrand factor. Those skilled in the art will recognize that Factor XIII (FXIII) is a fibrin stabilizing factor, Factor VIII (FVIII) is an essential blood clotting factor, and von Willebrand factor is a blood glycoprotein involved in hemostasis.

Fibrin gel as a cell encapsulating material allows for the formation of a three-dimensional vascularized tissue. In accordance with the present invention, we found that the concentration of fibrin affects cell growth and organization. Fibrin is a net of fibers (diameter in the order of nanometers). Higher concentrations of fibrin have been shown to generate a denser fibrin mesh which can interfere with cells' ingrowth inside the matrix. Thus, a more flexible matrix is advantageous for cells' growth. In addition, if the concentration of fibrin is too high, the fibrin solidifies too fast and the cells cannot be introduced into it. On the other hand, a fibrin structure which is too soft appears to lose its structural stability and does not provide a proper support for cells' growth. Thus, fibrin concentration appears to be an important factor affecting both the extent of cell growth and the extent of cell organization toward successful vascularization.

In the present invention, various concentrations of fibrinogen and thrombin were applied to provide the optimum conditions for the formation of blood vessel network in vitro and in vivo. A mixture of fibrinogen and thrombin in various concentrations allows controlling the biological and mechanical environment to which cells are exposed. For example, higher concentrations of fibrinogen create a more solid gel (macro-environment parameter), and variation in fibrinogen concentration affects fibers mesh thickness and density (micro environment parameter). Such variations in the three-dimensional environment affect tissue development and vascular network formation.

In certain embodiments, the fibrin gel is obtained from a mixture of fibrinogen at a concentration from about 1 to about 50 mg/ml and thrombin at a concentration from about 1 to about 300 U/ml. In certain embodiments, the fibrinogen concentration is selected from 1, 5, 15, or 50 mg/ml and the thrombin concentration is selected from 1, 50, 100 or 300 U/ml.

From the in vitro experiments we learned that in constructs with higher concentrations of fibrin, the degradation of fibrin was slower (as shown in FIGS. 5A-5F). Thus, if we want to keep fibrin in vivo for a longer time we have to use higher concentrations of fibrin. On the other hand, too high concentration of fibrin can be problematic since: (i) it will solidify too fast in vitro and will not provide sufficient time to encapsulate cells, and (ii) high concentration can interfere with cell growth and organization toward 3D vessel network.

In addition, the amount of total fibrin also has an effect on the vascularization process (with constant cell number). In the experiments, constructs with total fibrin in the amount of 60 µl (for fibrin alone) and 20 µl or 60 µl (for fibrin-PLLA/PLGA scaffolds) were examined. Our results show that the amount of 60 µl fibrin is preferable for cell growth and vascularization.

Suitable polymeric synthetic scaffolds for use in the present invention may be formed from biodegradable polymers including poly(lactic acid) (PLA), poly(glycolic acid) (PGA) and PLA-PGA co-polymers (PLGA). Additional biodegradable materials for use in the present invention include poly(anhydrides), poly(hydroxy acids), poly(ortho esters), poly(propylfumerates), poly(caprolactones), polyamides, polyamino acids, polyacetals, poly(glycerol sebacate) (PGS), biodegradable polycyanoacrylates, biodegradable polyurethanes and polysaccharides. The polymeric synthetic scaffold may also be made from non-biodegradable polymers including polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, and poly(ethylene oxide). Those skilled in the art will recognize that this is an exemplary, not a comprehensive, list of polymers appropriate for tissue engineering applications.

In certain embodiments, the polymeric synthetic scaffold is made of PLLA/PLGA (poly-l-lactic acid/polylactic-co-glycolic acid) or polyglycolic acid. In certain embodiments, the polymeric synthetic scaffold is a sponge comprising a 50:50 mixture of PLLA/PLGA or a mesh comprising polyglycolic acid.

As fibrin matrix has poor mechanical strength, a quality that has already been suggested to be critical for tissue formation and vascularization, combination with PLLA/PLGA scaffold presents an attractive scaffold candidate for vascular formation in vitro and for promotion of neovascularization in vivo. PLLA/PLGA scaffold has previously proven appropriate for cell growth with excellent and tunable mechanical properties and supportive of construct vascularization. We describe here the use of fibrin matrix alone on in combination with polymeric synthetic scaffold to support multicellular construct vascularization in vitro and to promote neovascularization and perfusion of the implant upon implantation.

PLA and PLA/PGA copolymers are particularly useful for forming the biodegradable synthetic scaffolds. The erosion of the polyester scaffold is related to the molecular weight and crystallinity of the polymer. The higher molecular weight polymers, e.g., weight average molecular weights of 90,000 or higher, result in polymer scaffolds which retain their structural integrity for longer periods of time; while lower molecular weight polymers, e.g., weight average molecular weights of 30,000 or less, result in shorter scaffold life. The molecular weight and crystallinity also influence the stiffness of the polymer scaffold. The tacticity of the polymer also influences the modulus. Poly(L-lactic acid) (PLLA) is isotactic, increasing the crystallinity of the polymer and the modulus of mixtures containing it. One skilled in the art will recognize that the molecular weight and crystallinity of any of the polymers discussed above may be optimized to control the stiffness of the scaffold. Likewise, the proportion of polymers in a co-polymer or mixture may be adjusted to achieve a desired stiffness.

The molecular weight, tacticity, and cross-link density of the scaffold may also be regulated to control both the mechanical properties of the scaffold and the degradation rate (for degradable scaffolds). The mechanical properties may also be optimized to mimic those of the tissue at the implant site. The shape and size of the final implant should be adapted for the implant site and tissue type. The scaffold may serve simply as a delivery vehicle for the cells or may provide a structural or mechanical function. The scaffold may be formed in any shape, for example, as particles, a sponge, a tube, a sphere, a strand, a coiled strand, a capillary network, a film, a fiber, a mesh, or a sheet.

The porosity of the scaffold may be controlled by a variety of techniques known to those skilled in the art. The minimum pore size and degree of porosity is dictated by the need to provide enough room for the cells and for nutrients to filter through the scaffold to the cells. The maximum pore size and porosity is limited by the ability of the scaffold to maintain its mechanical stability after seeding. As the porosity is increased, use of polymers having a higher modulus, addition of stiffer polymers as a co-polymer or mixture; or an increase in the cross-link density of the polymer may all be used to increase the stability of the scaffold with respect to cellular contraction.

The scaffolds may be made by any of a variety of techniques known to those skilled in the art. Salt-leaching, porogens, solid-liquid phase separation (sometimes termed freeze-drying), and phase inversion fabrication may all be used to produce porous scaffolds. Fiber pulling and weaving (see, e.g. Vacanti, et al., (1988) Journal of Pediatric Surgery, 23: 3-9) may be used to produce scaffolds having more aligned polymer threads. Those skilled in the art will recognize that standard polymer processing techniques may be exploited to create polymer scaffolds having a variety of porosities and microstructures.

The polymeric synthetic scaffold provides mechanical support for the cells, biocompatibility and controllable degradation. The fibrin gel as a cell supporting matrix for cells' seeding within PLLA/PLGA sponge allows for minimizing cells loss during the seeding procedure and provides biological cross-talk with cells and stimulation of angiogenesis in vitro and in vivo. The importance of the scaffold is to keep a constant size and to provide mechanical support (stability). If we use fibrin alone it shrinks due to forces inflected by cells. On the other hand, fibrin is a natural material and thus provides adhesion sites for cells.

The conventional method today for culturing cells within polymeric sponges is through Matrigel™, a soluble basement membrane matrix extracted from Engelbreth-Holm-Swarm mouse tumor cells. Matrigel™ is a material which becomes a gel at 37° C. and provides reasonable results but adds undesired animal contaminations and it is not approved by the FDA for clinical applications. Fibrin matrix based on fibrinogen and thrombin components which is derived from a human source, provides a productive environment for tissue formation and for vascularization.

The fibrin gel alone or in combination with PLLA/PLGA sponge can serve as a supporting three-dimentional matrix for the formation of various engineered tissues in vitro as well as for the integration of vascular network within the engineered tissue of choice. After formation in vitro, the three-dimentional construct is aimed to be transplanted in the damaged area in vivo to induce functional benefit on the host tissue. For example, this unique matrix can be utilized for the formation of engineered pancreatic tissue (for diabetic patients) or heart muscle tissue (for infarcted heart patients).

As used herein, the term "at least one type of vascular cells" refers to a cellular preparation of one type, two types, three types or more vascular cells. In certain embodiments, the at least one type of vascular cells is a co-culture comprising two types of vascular cells. In certain embodiments, the vascular cells are selected from endothelial cells and fibroblast cells. In certain embodiments, the endothelial cells are adult vein endothelial cells, adult artery endothelial cells, embryonic stem cell-derived endothelial cells, iPS-derived endothelial cells, umbilical vein endothelial cells, umbilical artery endothelial cells; endothelial progenitors cells derived from bone marrow, endothelial progenitors cells derived from cord blood, endothelial progenitors cells derived from peripheral blood, endothelial progenitors cells derived from adipose tissues. In certain embodiments, the umbilical vein endothelial cells are human umbilical vein endothelial cells (HUVEC). In certain embodiments, the fibroblasts are human foreskin fibroblasts, human embryonic fibroblasts, mouse embryonic fibroblasts, skin fibroblasts cells, vascular fibroblast cells, myofibroblasts, smooth muscle cells, or mesenchymal stem cells (MSCs)-derived fibroblast cells.

The tissue specific cells may be muscle cells, pancreatic beta cells, osteoblasts, chondrocytes, myoblasts, adipocytes, neuronal cells, glial cells, cardiomyocytes, liver cells, urethral cells, kidney cells, periosteal cells, bladder cells, odontoblasts, dental pulp cells, periodontal cells, tenocytes, lung cells, cardiac cells, skeletal cells, stem cell or iPS-cell derived tissue specific cells, and a combination thereof. In certain embodiments the tissue specific cells are muscle cells, pancreatic beta-islet cells, cardiomyocytes, liver cells, lung cells, neural cells, bone or kidney cells. By muscle cells is meant cardiomyocytes (human embryonic stem cells derived cardiomyocytes, iPS-derived cardiomyocytes or cardiac stem cells), smooth-muscle cells, myoblasts, skeletal muscle cells, and skeletal stem cells (satellite cells).

In certain embodiments, the three-dimensional fibrin engineered tissue construct comprises a combination of a co-culture of HUVEC and human foreskin fibroblast cells and myoblasts, wherein the cells are encapsulated within a three-dimensional fibrin gel and said fibrin gel is based on a mixture of fibrinogen and thrombin at a concentration enabling formation of blood vessel network in vitro and in vivo.

In certain embodiments, the three-dimensional fibrin engineered tissue construct comprises a co-culture of HUVEC and human foreskin fibroblast vascular cells or a combination of said co-culture and myoblasts, encapsulated within a hybrid scaffold of fibrin gel and a polymeric synthetic scaffold selected from a PLLA/PLGA sponge or a polyglycolic acid mesh.

In accordance with the present invention, it was found that three-dimensional (3D) constructs based on fibrin, or a hybrid scaffold of fibrin and a synthetic scaffold, embedded with various cellular populations (also termed herein "cellular preparations"), can promote tissue vascularization in vitro and in vivo.

In the present invention, two types of cellular preparations were examined for the production of three-dimensional fibrin-based constructs: (i) a co-culture of endothelial and fibroblast cells aimed at generating 3D endothelial vessel network, and (ii) a tri-culture preparation of endothelial, fibroblasts and myoblast cells for generating 3D vascularized skeletal muscle construct. Different concentrations of cells (endothelial cells, fibroblasts and myoblasts) in various combinations were used to obtain optimal vascularization.

These cellular preparations were embedded within a 3D fibrin construct alone or in combination with a synthetic scaffold. Synthetic scaffolds of PLLA/PLGA sponge or VICRYL™ mesh were used in this study as they are well characterized scaffolds in tissue engineering providing the adequate mechanical support, biodegradability and biocompatibility for the cellular culture. However, other synthetic scaffolds can be used and are encompassed by the present invention. Our results demonstrate that fibrin matrix alone or in combination with synthetic scaffold seeded with various cell types is a powerful strategy for induction of well-formed, intense vessel-like network. Transplantation studies show that this vascular network was successfully established in vivo and it promoted host blood vessels perfusion to the transplanted graft.

The two multicellular systems involving co-culture of endothelial cells and fibroblasts and tri-culture of myoblasts, endothelial cells and fibroblasts, were tested with respect to the following issues for their influence on vascularization process: (1) the effect of various thrombin and fibrinogen concentrations and quantities; (2) the effect of combining a synthetic PLLA/PLGA porous scaffold, (3) differentiation potential of fibroblasts and myoblasts, and (4) neovascularization and perfusion of the graft in vivo. These aspects will be discussed below in details. Several important notes should be delineated beforehand. First, the ratios between various cell types was determined upon our previous calibration experiments using the PLLA/PLGA scaffold (data not shown) in which ratios between 1:2 and 1:10 (1:5 was used in this study) of endothelial cells and HFF cells and a ratio of 1:1 between endothelial cells and myoblasts cells was found proper for vascularization and tissue formation. Second, the amount of cells that was used ($0.3/0.06*10^6$ for EC/fibroblasts and $0.3/0.3/0.06*10^6$ for myoblasts/endothelial cells/fibroblasts) is in accordance with our previous cell density optimization experiments using PLLA/PLGA scaffolds. These cell densities are much higher than those usually described in the literature, but were shown to provide excellent results with other systems and are certainty more clinically appealing. Lastly, in this study we analyzed two different cellular assays (endothelial cells/HFF and C2/endothelial cells/HFF), in each we used the same amount of endothelial cells and HFF, so total cell density was much higher in the tri-cultures due to adding myoblast cells. As such, it is believed that direct comparisons between these two systems are inappropriate, and each cellular system should be separately analyzed and discussed (the alternative could have been to reduce the amount of endothelial cells and HFF so the total cell amount will be constant).

Effect of thrombin and fibrinogen concentrations in vitro: In depth analysis of vessel network formation during in vitro cultivation was executed using advanced confocal large field analysis in which 3D vessel network organization could be easily detected.

Vessel network was quantitatively evaluated in two aspects: (1) network maturity levels (as determined by the four patterns and colors, FIGS. 8E-8H), and (2) vascular morphology assessment (vessel length and thickness, FIGS. 10A-10D). In this regard, full connectivity of a network is desired since potentially a single anastomosis between implanted and host vessels upon implantation could provide perfusion to the entire graft.

Figure 4A:
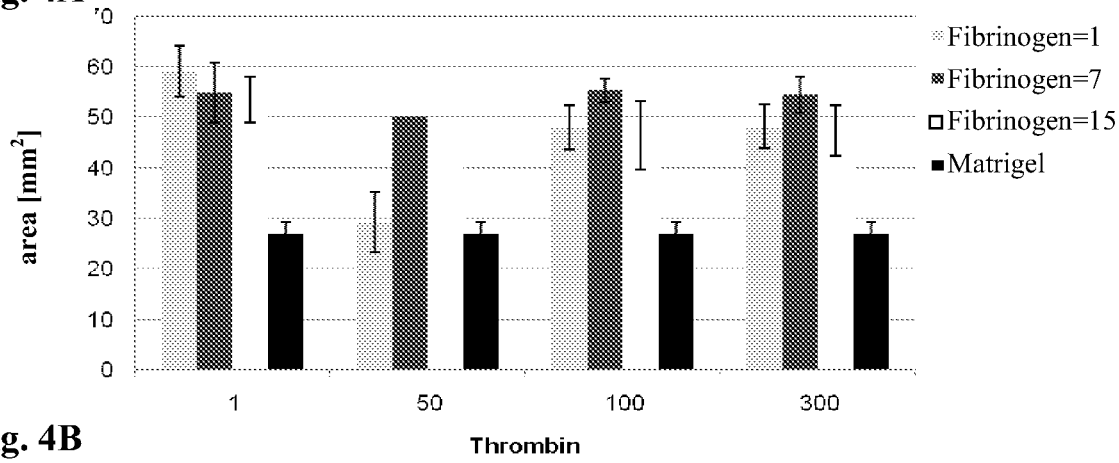
FIGS. 4A-4C show quantification of the vascularization process for various fibrin concentrations of fibrinogen (1, 7, 15 mg/ml) and thrombin (1, 100, 300 U/ml). (4A) % endothelial area, (4B) blood vessel length and (4C) blood vessel thickness. For higher fibrinogen concentrations, endothelial cells coverage was higher (4A) and the endothelial sprouts became thinner (4C) and elongated (4B). This tendency was similar in all thrombin concentrations tested. Quantification was performed using endothelial antibody CD31.
Figure 4B:
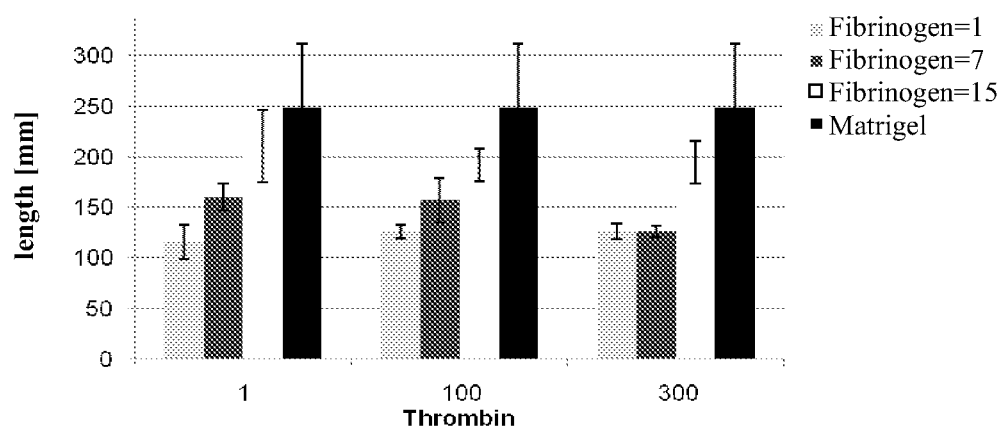
Figure 4C:
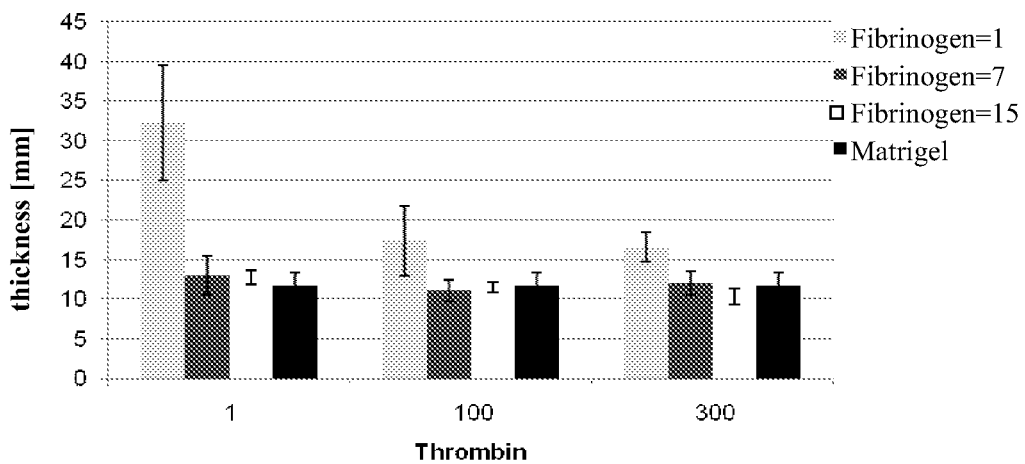
Figure 9A:
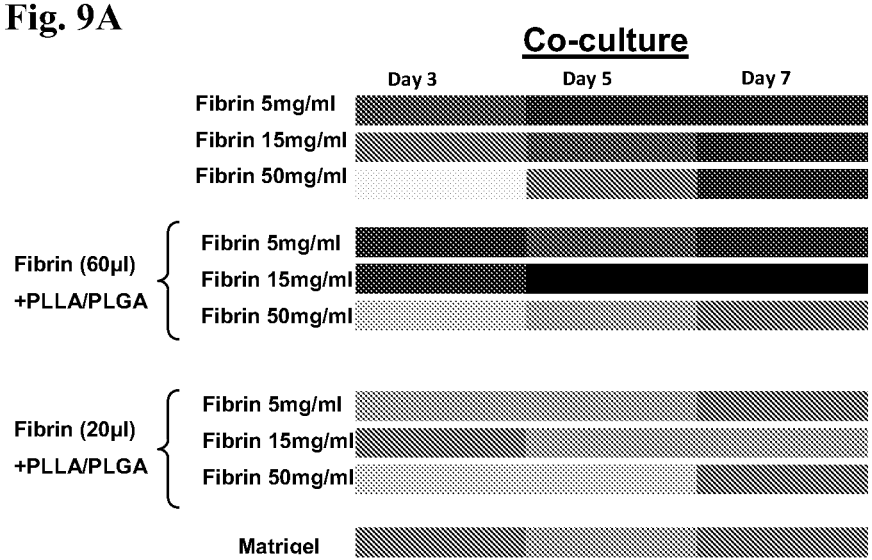
FIGS. 9A-9B show quantification of vessel network levels at 3, 5 and 7 days from cell seeding for fibrin constructs (5, 15 and 50 mg/ml fibrinogen) and fibrin+PLLA/PLGA constructs (5, 15 and 50 mg/ml fibrinogen and fibrin quantity of 60 μl or 20 μl) embedded with either a co-culture of endothelial and fibroblasts cells (9A) or a tri-culture containing endothelial, myoblasts and fibroblast cells (9B).
Figure 9B:
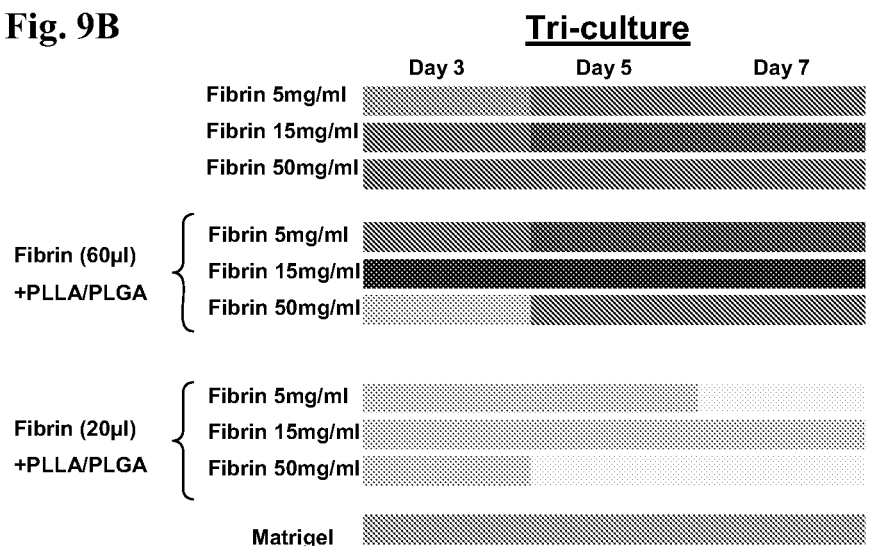

Early experiments determined that thrombin concentrations had no effect on the vascularization process FIGS. 4A-4C, but only on polymerization kinetics. On the contrary, vessel network formation in 3D fibrin constructs showed tight dependence on fibrinogen concentrations (FIGS. 4A-4C). Network levels analysis revealed that the process of network organization is highly regulated by fibrinogen concentrations. For the co-cultures, although they shrank dramatically, fibrin constructs reached high level of network connectivity after 7 days in culture (FIG. 9A); and the kinetics of this process was augmented for lower fibrinogen concentrations. For the tri-cultures, low degree of network organization was observed for all fibrinogen concentrations tested, and the highest levels were detected for the 15 mg/ml fibrinogen concentration providing partially connected vessel network (FIG. 9B). It is possible that the high cell densities in the tri-cultures constructs impeded vascular formation by the endothelial cells.

Network morphology assessment of fibrin constructs after 7 days in culture revealed interesting dependence on fibrinogen concentrations. For the co-culture, clear tendency toward thinner and elongated vessels was observed for elevated fibrinogen concentrations. For the tri-cultures, a pick value at fibrinogen concentration of 15 mg/ml was detected in which long and thick vessels were formed.

Figure 2A:
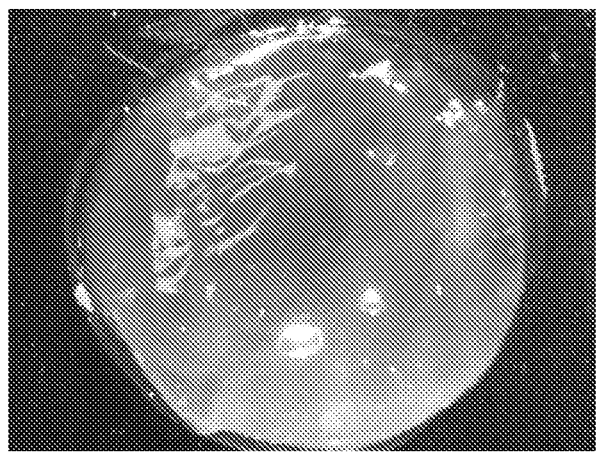
FIGS. 2A-2C show the different scaffolds used as support for the cellular preparations. (2A) Fibrin construct; (2B) PLLA/PLGA construct and (2C) Fibrin+PLLA/PLGA construct.
Figure 2B:
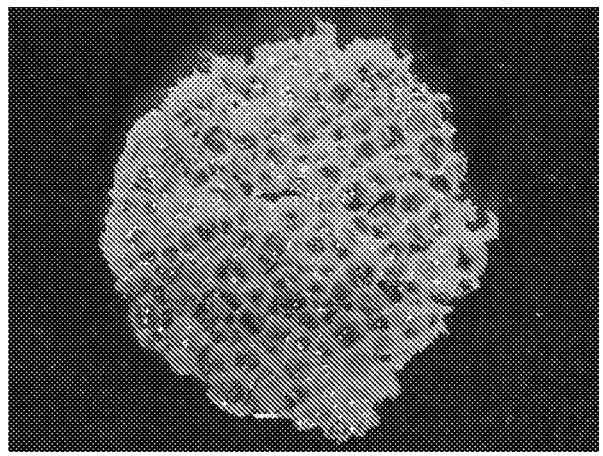
Figure 2C:
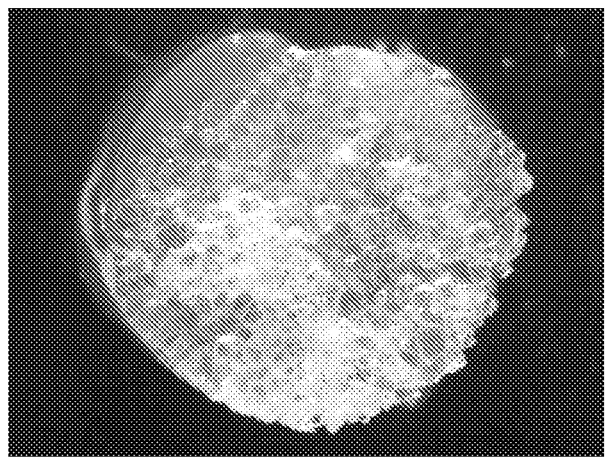

Effect of adding PLLA/PLGA scaffold to fibrin matrix in vitro: In vitro network formation within the combined fibrin+PLLA/PLGA constructs was examined under various fibrinogen concentrations (5, 15 and 50 mg/ml as before), and using two fibrin quantities (total volume of 20 and 60 μl fibrin). In the volume of 60 μl, the PLLA/PLGA scaffold was completely embedded within a fibrin gel (FIG. 2C). When a volume of 20 μl was used, fibrin only filtrated into scaffold pores (image is not shown). The results clearly indicate that a volume of 60 μl is preferable for co- and tri-cultures vascularization processes, as can be easily seen by the decrease in network levels (reduction in color intensities, FIGS. 9A and 9B). Hence, discussion will address only on the 60 μl-containing constructs. Fibrinogen concentrations influenced both network levels and morphology. The highest level of network connectivity was observed in the fibrin+PLLA/PLGA scaffolds picked at fibrinogen concentration of 15 mg/ml (for the co- and tri-culture conditions, FIGS. 9A and 9B). After 1 week in culture, for the co-cultures, thicker and longer vessels appeared to form when elevated fibrinogen concentration were used. In the tri-cultures, again at a pick value of 15 mg/ml fibrinogen concentration was detected in which long and thick vessels were formed.

Overall, combining PLLA/PLGA with fibrin matrix maintained constant construct size for the entire culture time, resulting in spreadable and openly distributed vessels networks (FIGS. 7E-7H). At an optimal fibrinogen concentration of 15 mg/ml full-connected vessel network was generated.

Figure 11A:
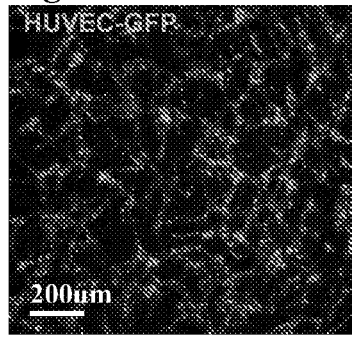
FIGS. 11A-11G show confocal image projections of whole fibrin or fibrin+PLLA/PLGA constructs embedded with a co-culture of endothelial and fibroblasts cells, wherein HUVEC cells were labeled with GFP (11A and 11C, green signal) and the constructs were immunofluorescently stained after 7 days with αSMA antibody demonstrating the presence of smooth muscle-like cells (11B and 11D, red signal). Double staining for VWF (endothelial maker) and αSMA on cross-sections revealed the presence of smooth muscle cells and their localization around endothelial lumen vessels (11E-11G, higher magnification).
Figure 11B:
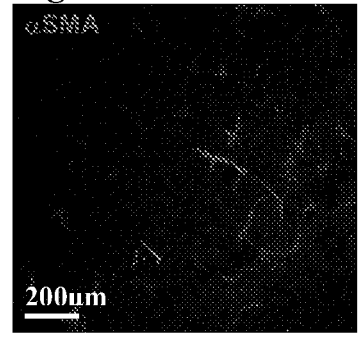
Figure 11C:
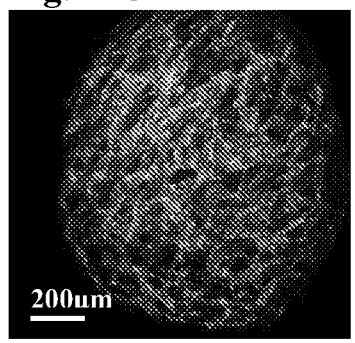
Figure 11D:
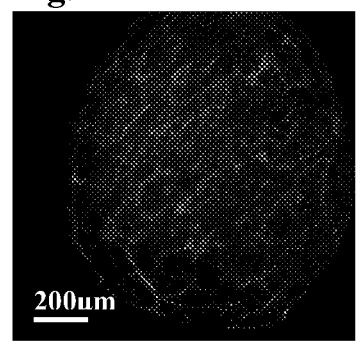
Figure 11E:
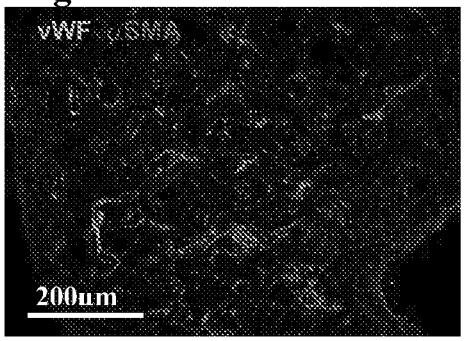
Figure 11F:
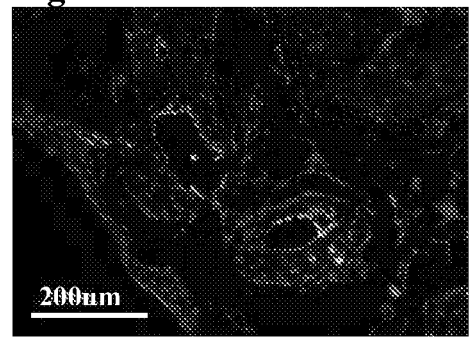
Figure 11G:
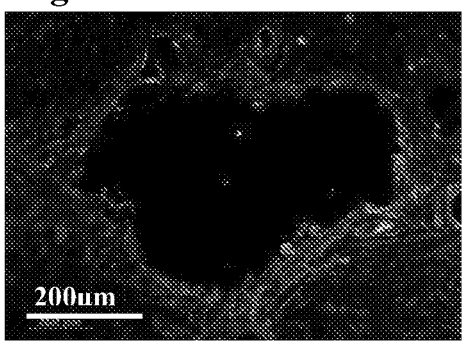

Differentiation of fibroblast and myoblasts: It has been demonstrated that fibroblast cells promote vascularization through secretion of angiogenic growth factor, or through differentiation into mural cells which afford direct physical contact to endothelial cells. The data presented supports the concept that fibroblasts can differentiate into smooth muscle-like cells within 3D fibrin rich environment providing physical support while recruiting and covering the endothelial vessels in vitro (FIGS. 11E-11G).

In addition, in the tri-culture preparations, the myoblast cells were shown to form partially aligned long myotubes (FIGS. 11C and 11D), a desired phenomenon for construction of skeletal tissue construct. Differentiation dependence on fibrinogen concentrations and/or the presence of PLLA/PLGA scaffold wasn't protruded in our experiments.

In vivo transplantation studies: To primarily determine the impact of PLLA/PLGA scaffold when added to fibrin matrix on neovascularization and perfusion of the graft, we implanted four groups of constructs: fibrin, and fibrin+PLLA/PLGA acellular constructs or co-delivered with HUVEC and HFF cells. One of the major challenges in such procedures is to quantitatively evaluate graft perfusion and neovascularization outcomes. We show here that our novel in vivo model provides a suitable assay to calculate the area of functional blood vessels penetrating the graft. Also, it enabled to easily detect graft size. Graft size that maintains mechanical stability and adequate size in vivo is advantageous as in many therapies, such as heart regeneration, the implanted construct should resist to external forces and provide mechanical support to the injured tissue. The data presented show that addition of PLLA/PLGA scaffolds to fibrin matrix increase graft area, and plays a significant role in promoting neovascularization and perfusion of the implant in vivo. A significant enlarged area of FITC-Dextran$^+$ vessels entering the implant was observed in constructs containing PLLA/PLGA. Surprisingly, in contrast to our previous studies and of others, we did not note any significant difference between cellular and acellular constructs. It might be possible that the impact of cells did exist but was not visible under the considerable effect contributed by addition of PLLA/PLGA scaffold.

RFP-expressing endothelial cells provided for in vivo tracing of implanted cells, while vascular perfusion of FITC-dextran aided in identification of functional mouse- and human-derived blood vessels in the graft area. To date, most of previous studies dealing with vascularization in vivo analyzed only histological cross sections of the implanted cells, which were shown to form CD31+ lumens in the graft area (CD31 is a specific marker for human endothelial cells). However, an interesting and important aspect is to resolve the spatial 3D organization of the network in vivo. In our systems, we observed 3D inter-connected vessel network lined by HUVEC-RFP cells. This remarkable organization was profoundly detected in the fibrin and fibrin+PLLA/PLGA constructs when compared to PLLA/PLGA constructs. Also, the total human cellular DNA was augmented in these two fibrin-based constructs (fibrin and fibrin+PLLA/PLGA) when compared to implanting only PLLA/

PLGA scaffold without fibrin. That result provides evidence for the necessity of fibrin matrix for cell retention in vivo.

Careful examination of the implant-host integration area demonstrated close interactions between vessels formed by implanted endothelial cells and host neovessels invading the implant area, as well as the presence of mosaic implant/host vessels. However, the exact mechanism of inosculation and the interaction of implanted and host neovessels, still remains to be worked on in more details. Importantly, although FITC-Dextran was not evident within the implanted HUVEC vessels, bright field images of the implanted-cellular constructs (fibrin, fibrin+PLLA/PLGA, and PLLA/PLGA) revealed that blood circulation did flow through them in some point of engraftment.

In another aspect, the present invention relates to a method for the preparation of the three-dimensional fibrin engineered tissue construct of the invention, comprising the steps:
 (i) mixing vascular cells or a combination of said vascular cells and tissue specific cells with a thrombin solution and transferring the thrombin-cell suspension to a silicone tube mold that may contain a polymeric synthetic scaffold at the bottom;
 (ii) adding a solution of fibrinogen to the silicone tube mold and mixing for a short period;
 (iii) incubating the silicone tube mold to allow polymerization of the fibrinogen; and
 (iv) removing the silicone tubes and adding a cell medium, thus obtaining the desired fibrin construct.

For the preparation of a fibrin gel matrix embedded with a combination of at least one type of vascular cells and tissue-specific cells, the method comprises the steps:
 (i) mixing a combination of at least one type of vascular cells and tissue specific cells with a thrombin solution and transferring the thrombin-cell suspension to a silicone tube mold;
 (ii) adding a solution of fibrinogen to the silicone tube mold and mixing for a short period;
 (iii) incubating the silicone tube mold to allow polymerization of the fibrinogen; and
 (iv) removing the silicone tubes and adding a cell medium, thus obtaining the desired fibrin construct.

For the preparation of a hybrid scaffold of fibrin gel and a polymeric synthetic scaffold comprising at least one type of vascular cells or a combination of at least one type of vascular cells, and tissue-specific cells, the method comprises the steps:
 (i) mixing at least one type of vascular cells or a combination of at least one type of vascular cells, and tissue specific cells with a thrombin solution and transferring the thrombin-cell suspension to a silicone tube mold that contains a polymeric synthetic scaffold at the bottom;
 (ii) adding a solution of fibrinogen to the silicone tube mold and mixing for a short period;
 (iii) incubating the silicone tube mold to allow polymerization of the fibrinogen; and
 (iv) removing the silicone tubes and adding a cell medium, thus obtaining the desired construct based on a hybrid scaffold of fibrin gel and a polymeric synthetic scaffold.

The term "short period" with respect to the "mixing" refers to a period of several seconds, preferably 2-5 seconds, more preferably 3-4 seconds. The duration of incubation for the polymerization of the fibrinogen and formation of the construct may range from 30 min-90 min and is preferably 30 min or 60 min.

The three-dimensional fibrin engineered tissue construct can be implanted into any tissue in need of therapy, including connective, muscle, nerve, and organ tissues either directly/immediately after the removal of the silicon tube, or after further incubation in vitro. In vitro incubation periods can include a range between few hours (1-24 hr) to several days (1-7 days). Following incubation, a tissue with only blood-vessels is formed from the construct comprising only vascular cells and a three-dimensional engineered tissue comprising internal blood vessel network/architecture is formed from the construct comprising a combination of vascular cells and tissue specific cells.

The three-dimensional fibrin engineered tissue construct of the present invention may be applied to the area in need of treatment using any suitable route including, but not limited to, transplantation as exemplified herein in Example 7.

The scaffold supported cells of the present invention may be transplanted per se to a human subject, or in a pharmaceutical composition where it is mixed with suitable carriers or excipients.

In another aspect, the present invention relates to a pharmaceutical composition comprising the three-dimensional fibrin engineered tissue construct of the invention, composed of fibroblasts and endothelial cells, for use in treating ischemic tissues and for promoting vascularization.

In still another aspect, the present invention relates to a pharmaceutical composition comprising the three-dimensional fibrin engineered tissue construct of the invention composed of two types of vascular cells in combination with tissue specific cells, for generation of three-dimensional vascularized tissue construct for transplantation.

In certain embodiments, the vascular cells are endothelial cells and fibroblasts and said tissue specific cells are muscle cells, e.g., myoblasts or myocytes, for generation of three-dimensional vascularized muscle construct for transplantation.

The pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

The pharmaceutical compositions for use in accordance with the present invention may thus be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

The three-dimensional vascularized tissue construct may be used for example in filling a deficient tissue, treating injured or damaged tissue and for treating ischemic tissues. More specifically, the vascularized tissue construct can be used in treatment of diseases and disorders selected from: brain diseases (e.g. Parkinson's disease), cornea diseases, liver disorders (e.g. metabolic disorders, liver cirrhosis, liver cancer), pancreas disorders (diabetes), muscle disorders (muscle injury, cardiac disease, muscular dystrophy), kidney diseases, vascular diseases (by replacement of large and small blood vessels), ligament and tendon diseases, bone disorders (in joint replacement, bone graft etc), cartilage disorders (e.g. meniscal tears, patella resurfacing, chondromalacia patellae, arthritis etc), burns and wounds, and for repair of damaged nerve (e.g. following spinal cord injury), trachea, esophagus, intestine, and urethra (Langer et al, 1993).

The vascularized tissue construct can also be used as a unique in vitro 3D model for several pathophysiological and pharmacological studies.

The three-dimensional vascularized muscle construct may be used for example in filling a deficient muscular tissue, treating injured or damaged muscle tissue, and coverage of exposed bones.

A culture of multiple cell types, i.e. vascular cells (endothelial and fibroblast cells) and tissue specific cells (muscle cells, pancreatic beta cells etc) encapsulated in the three-dimensional fibrin matrix, or in a combination of fibrin with a polymeric scaffold (e.g. PLLA/PLGA) allows to mimic the native cellular environment, provide the adequate interactions between cells (growth factors and cytokine secretion), and result in increased maturation, differentiation and vascularization of the construct (as previously reported in Levenberg et al., 2005, Caspi et al., 2007, Lesman et al., 2010).

The present invention will now be described in more detail in the following non-limiting Examples and the accompanying figures.

EXAMPLES

Materials and Methods (i) Cell culture:

1. Human Umbilical Vein Endothelial Cells (HUVECs): HUVECs (passage 3-6, Clonetics™, from Lonza Cologne GmbH) were grown on tissue culture plates in EGM-2 medium supplemented with 2% FBS and endothelial cell growth medium BulletKit®-2 (EGM-2® BulletKit®). To closely monitor the temporal development of vascularization in vitro and in vivo, HUVECs expressing fluorescent markers (labeled HUVEC-GFP and HUVEC-RFP, Angio-Proteomie, USA) were used.

2. Human Foreskin fibroblast cells (HFF): Primary culture of HFF cells were prepared in our laboratory from newborn's foreskin and used until passage 20. HFF cells were cultured in medium consisting of DMEM supplemented with 10% FBS, 1% NEAA (Non-Essential Amino Acids), and 0.2% β-mercapthoethanol.

3. C2 cell line: C2 myoblast cells were maintained in DMEM (high glucose, with glutamine) supplemented with 20% FBS (v/v), 2.5% HEPES (v/v) and 1% Pen strep (v/v).

(ii) Multicellular preparations: Two multicellular preparations were examined: (i) co-culture preparation of endothelial (HUVECs, $0.3*10^6$ cells) and fibroblasts cells (HFF cells, $0.06*10^6$) aimed at generating 3D vascular network, and (ii) a tri-culture preparation of endothelial (HUVECs, $0.3*10^6$ cells), myoblast cells (C2, $0.3*10^6$ cells), and fibroblasts (HFF, $0.06*10^6$) aimed at generating 3D vessel network embedding within skeletal muscle construct.

(iii) Preparation of fibrin gel: fibrin gel (FIG. 2A) was prepared from a combination of fibrinogen (Biological Active Components 2 (BAC2) containing: 70 mg/ml fibrinogen, 10 mg/ml fibronectin, 15 mg/ml IgG, 5 mg/ml albumin, 10 micg/ml plasminogen, 7 micg/ml FXIII, 1 micg/ml FVIII, 7 micg/ml von Willebrand (the rest of the proteins are in the concentration of the plasma proteins); EVICEL Fibrin Sealant (Human), Johnson & Johnson— Wound Management, Somerville, N.J.) and thrombin (1000 U/ml purified-plasma thrombin).

(iv) Preparation of PLLA/PLGA scaffold: Porous sponges composed of 50% poly-l-lactic acid (PLLA) and 50% poly-lactic-co-glycolic acid (PLGA) were fabricated utilizing a particulate leaching technique to achieve pore sizes of 212-600 μm and 93% porosity (as described in Mooney et al., 1997). Briefly, PLLA (Polysciences) and PLGA (Boehringer Ingelheim) 1:1 were dissolved in chloroform to yield a solution of 5% (wt/vol) polymer; 0.24 ml of this solution was loaded into molds packed with 0.4 gr of sodium chloride particles. The solvent was allowed to evaporate, and the sponges were subsequently immersed for 8 hr in distilled water (changed every hour) to leach the salt and create an interconnected pore structure. The PLLA/PLGA 50/50 sponges, which had an average pore diameter of 250 μm, were designed to be circular with diameter of 6 mm and thickness of 1 mm (obtained by cutting with a puncher, FIG. 2B). Before transplantation, sponges were soaked in 70% (vol/vol) ethyl alcohol overnight and washed three times with PBS. Previous work demonstrated the biocompatibility of PLLA/PLGA porous scaffold and estimated that its degradation time is about 6 months (Holder et al., 1998). Combination of fibrin matrix and PLLA/PLGA synthetic sponge in all fibrin concentrations tested, resulted in homogeneously spread fibrin gel throughout the PLLA/PLGA pores (FIG. 2C).

(v) Preparation of VICRYL™ mesh: Vicryl™ (polyglactin 910) is an absorbable, synthetic, braided suture, manufactured by Ethicon Inc., a subsidiary of Johnson and Johnson. VICRYL™ is completely absorbed by hydrolysis within 70 days (FIG. 6A).

(vi) Immunofluorescent staining:

1. Staining of Paraffin sections: In vitro tissue-constructs were fixed in 10% formalin for 6 hrs before tissue processing (at our lab). 5 μm thick transverse sections were cut and placed on slides for immunofluorescence staining or hematoxyline and eosin (H&E) staining. For immunofluorescence staining, primary and secondary antibodies plus DAPI were prepared using the dilutions as follows. For epitope recovery, prior heat treatment at 60° C. for 30 min followed by treatment at 95° C. for 20 min in Reveal buffer (Biocare Medical, Concord, Calif.) within a pressure cooker was performed. For immunofluorescence staining, primary and secondary antibodies plus DAPI were prepared using the following dilutions. Primary antibodies: monoclonal anti human CD31 (1:80, Cell Maque), polyclonal anti-vWF (1:200); monoclonal anti a-smooth muscle actin (1:50), and monoclonal anti-Desmin (1:150) (all from Dako). Secondary antibodies: Cy3-conjugated anti-mouse IgG (1:100) (Jackson Immunoresearch Laboratory, Pa.); and AlexaFluor 488 conjugated anti mouse IgG (1:100) (Molecular Probes). Nuclei were counterstained using DAPI (Sigma). For mounting, Fluromount-G and cover slips were used to protect the sections.

2. Staining of whole construct: Entire constructs were immunofluorescently stained. The scaffolds were fixated using 4% paraformaldehyde for 10 min and subsequently washed in PBS. The cells underwent permeabilization using 0.3% Triton X-100 for ten minutes in room temperature. The scaffolds were then washed in PBS, and immersed in blocking serum (10% FBS, 0.1% Triton X-100, 1% glycine) overnight at 4° C. Primary antibodies were then added (as detailed above, immersed in the blocking serum) and the scaffolds were incubated overnight at 4° C. Following several washes in PBS, the secondary antibodies were applied for three hours. After final washes in PBS, the scaffolds were kept in 24-wells plate in PBS at 4° C. until examined under the confocal microscope.

(vii) Transplantation of the fibrin-based tissue constructs: All surgical procedures were conducted according to protocols approved by the Institutional Animal Care and Use Committee. For the implantation procedure, fibrin-based constructs were prepared with co-cultures of HUVEC-expressing RFP ($0.3*10^6$ cells) and HFF ($0.06*10^6$ cells), incubated for 1 hour in vitro and then implanted as follows. 8 weeks old male nude mice (Harlan Laboratories, Rehovot, Israel) were anesthetized using a ketarnine/xylazine cocktail at a dose of 35 µl/20 g delivered with 25-gauge needle. A small incision was made allowing access to the linea-alba and surrounding tissue, where a 3×2 mm full defect segment was removed. Fibrin-based constructs were sutured in place using four 8-0 silk sutures. All mice were monitored closely for 1-2 hours to ensure full recovery from the anesthesia. 1 week, 10 days or two weeks later, mice were anesthetized again and 10 mg/ml FITC or Rhodamine-Dextran (Sigma, Rehovot, Israel) was perfused through the tail vein for 10-20 sec before euthanization. The graft area was dissected and fixated with formalin 10%. Immediately afterwards, the implanted area was imaged using the confocal microscope, paraffin embedded or proceeded to DNA extraction.

(viii) Confocal imaging: For construct cross-sections imaging, the Inverted Zeiss Microscope (Zeiss MTB2004, Carl Zeiss, Germany) was used, with pictures taken in two CCD cameras (AxioCam MRm and AxioCam MRc5). Lenses in use were: ×4, ×10, ×20, ×40 (oil).

For whole construct in vitro and implanted tissue from in vivo studies, the Leica™ TCS LSI macro confocal was used. This microscope provides 3D navigation through the specimen in high resolution and with a large field of view.

(ix) Quantification of vessel networks:

1. In vitro network maturity levels: we identified four different patterns of vessel networks and quantified the resulting 3D confocal projection images according to them. These patterns include: individual cells, multi-cellular groups of cells (not connected), partially connected vessel network, and fully connected vessel network (FIGS. 8E, 8F, 8G and 8H). We consider these patterns to be part of vascular development in its simplest manner: capillary formation, branching, and sprouting. Each specific pattern obtained a color, so there is a direct correlation between the network organization state and color intensity—the greater the intensity of the color, the vessel network is more developed. Four independent constructs were analyzed at total magnification for each condition (n=4).

2. In vitro network morphology (vessel length and thickness): 3D confocal projection images followed a series of image analysis using NIH ImageJ program to manually determine vessel length and thickness. Vessel length was calculated between proximity branches. Vessel thickness was calculated in the middle of each sprout, usually highlighted by a narrower region. Four independent constructs were analyzed at total magnification for each condition (n=4).

3. In vivo network quantification: To quantify total network length and area density of implanted HUVEC-RFP+ vessels, advanced automated computer program was used (in collaboration with Professor Z. Kam, Weizman Institute of Science, Israel), which allowed to locate vessel tubes using unique algorithm and determine their length and area density (6-9 confocal projection images at total magnification were analyzed for each condition).

(x) Statistical analysis: All results are reported as mean±standard derivation. Statistical comparison between two groups was done by Student's t-test. Results were considered significant for $p<0.05$.

Example 1

Preparation of 3D Fibrin Constructs

Preparation of fibrin-based tissue constructs: To prepare the fibrin-based constructs, the multicellular preparations consisting of co-culture/tri-culture cellular preparations ($0.3*10^6$ HUVECs and $0.06*10^6$ HFF cells, or in combination with $0.3*10^6$ C2 myoblast cells as detailed in Materials and Methods, section (ii) above) were first mixed with thrombin (purified from human plasma, stoke concentration of 1000 U/ml, Omrix Biopharmaceuticals, Ltd, Israel) inside a silicon mold positioned on top of a glass slide. Then, the fibrinogen solution (Biological Active Components 2, human source, stoke concentration of 70 mg/ml, Omrix Biopharmaceuticals, Ltd, Israel) was added to the mold by employing pipette mixing. The constructs were allowed to polymerize for 30 min inside the incubator (37° C., 5% $CO_2$, high humidity) and then the silicone mold was gently removed. The construct was placed in a 6-well non-tissue culture plate and 4 ml of medium consisting of 50% HUVEC medium and 50% C2 medium was added to each well. Medium was changed every other day. For control assay, the multicellular preparations were embedded in Matrigel™ (BD Biosciences) and followed the same construct procedure.

Various biomaterial parameters were tested for their influence on the vascularization process including:

(i) Fibrin concentration: fibrinogen precursor solutions of: 1, 5, 15, 50 mg/ml concentrations, and thrombin precursor solutions of: 1, 50,100,300 Units concentrations were examined.

(ii) Fibrin quantity: 20 µl (10 µl thrombin+10 µl fibrinogen) and 60 µl (30 µl thrombin+30 µl fibrinogen) providing cell concentrations of $18*10^6$/ml and $6*10^6$/ml for the co-cultures or $33*10^6$/ml and $11*10^6$/ml for the tri-cultures respectively.

(iii) Addition of a synthetic PLLA/PLGA scaffold to the fibrin matrix.

The fibrin based constructs were grown for 1 week in vitro and then proceeded to histological paraffin sectioning or whole scaffold imaging. For in vivo transplantation studies, the fibrin constructs were grown for 1 hour in vitro, and then proceeded to transplantation.

Example 2

Preparation of 3D Fibrin-PLLA/PLGA or Fibrin-VICRYL™ Construct

The PLLA/PLGA 50/50 sponges or VICRYL mesh were designed to be circular with diameter of 6 mm and thickness of about 1 mm (obtained by cutting with a puncher). For sterilization, PLLA/PLGA scaffolds were incubated overnight in 70% ethanol. VICRYL™ mesh was obtained sterile.

To make the fibrin-PLLA/PLGA or fibrin-VICRYL™ constructs, the desired concentrations of fibrinogen and thrombin were prepared. The PLLA/PLGA or VICRYL™ scaffold was placed in the bottom of each sterilized silicon mold (tubes with open ends, 6 mm in diameter). Cells' pellets, each consisting of $0.3*10^6$ HUVEC's and $0.06*10^6$ HFF cells (co-culture preparation), or additionally containing $0.3*10^6$ C2 cells (tri-culture preparation), were mixed with 300 of thrombin solution inside an Eppendorf™ tube. Then, the thrombin-cell mixture was carefully pipetted up and down a few times on the PLLA/PLGA or VICRYL™ scaffold, so that the mixture pushed through the scaffold pours. Air bubbles were avoided. Fibrinogen (30 µl) was then added to each scaffold and carefully pipetted up and down a few seconds. The mold containing PLLA/PLGA or VICRYL™ scaffold and fibrin with cells was placed in the incubator for 30 min to let the fibrinogen polymerize, after which the silicon tubes were gently removed and medium (50% C2 medium and 50% HUVEC medium) was added to each construct. Fibrin-PLLA/PLGA or fibrin-VICRYL™ constructs were grown for 1 week in vitro and then proceeded to histological paraffin sectioning or whole scaffold imaging. For in vivo transplantation studies, the fibrin-PLLA/PLGA constructs were grown for 1 hour in vitro, and then proceeded to transplantation.

Example 3

Effect of Various Concentrations of Fibrinogen and Thrombin on Vascularization in Fibrin Constructs Fibrin constructs comprising co-culture of endothelial and fibroblast cells according to Example 1 were prepared with various fibrinogen and thrombin concentrations. Fibrinogen concentrations tested were: 1, 7 and 15 mg/ml. Thrombin concentrations tested were: 1, 50, 100, 300 U/ml. The vascularization process in constructs containing fibrinogen concentrations of 1, 7 and 15 mg/ml, and thrombin concentrations of 1 and 100 is shown in FIGS. 3A-3B.

Figure 3A:
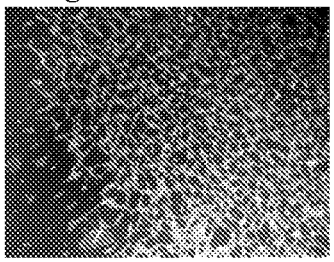
FIGS. 3A-3I show confocal imaging of co-culture of endothelial and fibroblast cells within various concentrations of fibrinogen and thrombin plated on top of tissue-culture dishes, in a low magnification of ×40 (3A-3C) and in a higher magnification of ×100 (3D-3I). Fibrinogen concentrations tested were: 1, 7 and 15 mg/ml (3A, 3B and 3C; 3D, 3E and 3F; 3G, 3H and 3I, respectively), thrombin concentrations tested were: 1, 50, 100, 300 U/ml, the concentrations shown are 1 U/ml (3A, 3B, 3C, 3D, 3E and 3F) and 100 U/ml (3G, 3H and 3I). Intense vessel network with many interconnected sprouts was formed in all cases (CD31 staining). The thickness, length and area covered by endothelial cells differ for various fibrin concentrations, with a clear tendency toward thinner and elongated sprouts in higher fibrinogen concentrations. It can be observed that thrombin concentrations had almost no effect on the vascularization process.
Figure 3B:
Figure 3C:
Figure 3D:
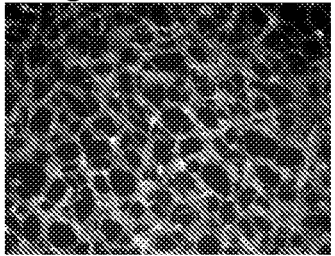
Figure 3E:
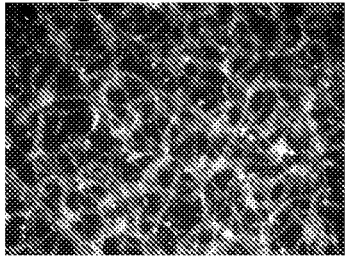
Figure 3F:
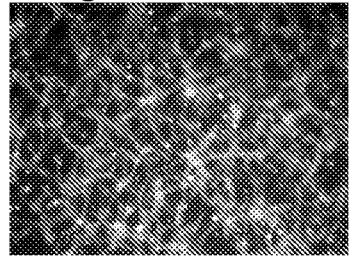
Figure 3G:
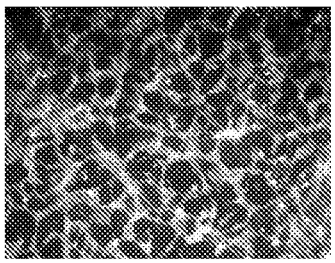
Figure 3H:
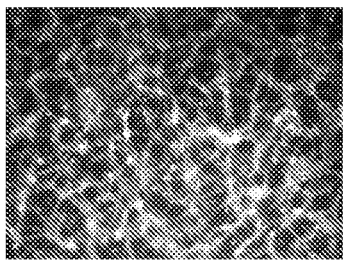
Figure 3I:
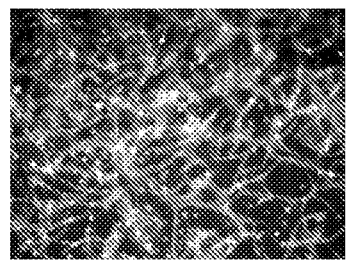

As can be seen in FIGS. 3A and 3B, intense vessel network with many interconnected sprouts was formed in all tested concentrations of fibrinogen and thrombin. The thickness and length of the sprouts and the area covered by the endothelial cells differ for the various fibrin concentrations. Our results show a clear tendency toward thinner and elongated sprouts for higher fibrinogen concentrations (FIGS. 4B-4C), however, thrombin concentrations had almost no effect on the vascularization process as detected by the positive area, thickness and length of CD31+ vessels (FIGS. 4A-4C). Thus, thrombin precursor solution of 50 mg/ml was selected in all subsequent in vitro and in vivo experiments.

Example 4

3D Fibrin-PLLA/PLGA and Fibrin-VICRYL™ Constructs

Figure 5A:
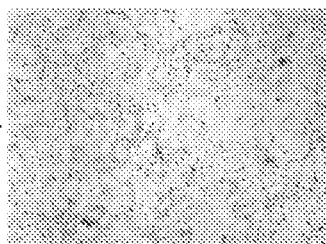
FIGS. 5A-5F show histological hematoxylin and eosin (H&E) sections of 3D fibrin-PLLA/PLGA constructs. Fibrinogen concentrations tested were: 1, 15 and 50 mg/ml for 5A, 5B and 5C; and 5D, 5E and 5F, respectively (thrombin concentration was constant, 50 U/ml). Lower magnification images (×4, 5A, 5B and 5C), and higher magnification images (×10, 5D, 5E and 5F), are shown. PLLA/PLGA scaffold substances and traces of fibrin matrix are observable as indicated by the arrows (5E). It can be clearly seen that for higher fibrinogen concentrations, the degradation of the fibrin was slower and higher amount of fibrin matrix was present throughout the PLLA/PLGA scaffold (5C and 5F). When the concentration of fibrinogen was 1 mg/ml, fibrin could not been observed (full degradation 5A and 5D).
Figure 5B:
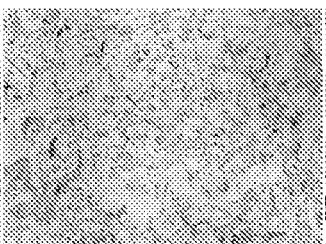
Figure 5C:
Figure 5D:
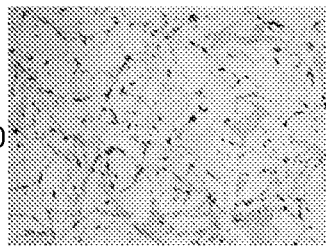
Figure 5E:
Figure 5F:
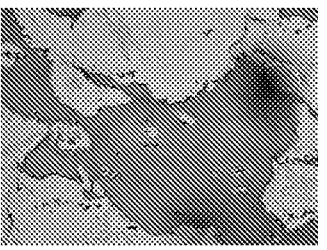
Figure 7A:
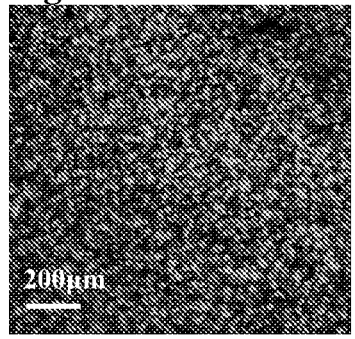
FIGS. 7A-7H show images of fibrin constructs (5 mg/ml fibrinogen, 7A-7D) and fibrin+PLLA/PLGA constructs (15 mg/ml fibrinogen, 7E-7H) embedded with co-culture preparations following 1, 3, 5 and 7 days from cell seeding (7A, 7B, 7C, 7D and 7E, 7F, 7G, 7H, respectively). HUVECs were labeled with GFP (green).
Figure 7E:
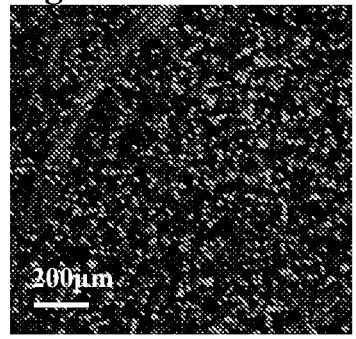
Figure 7B:
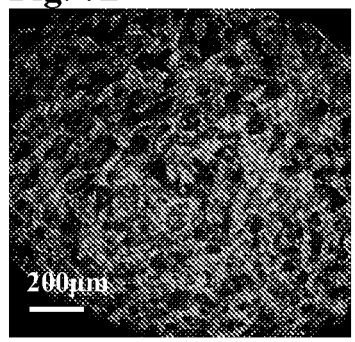
Figure 7F:
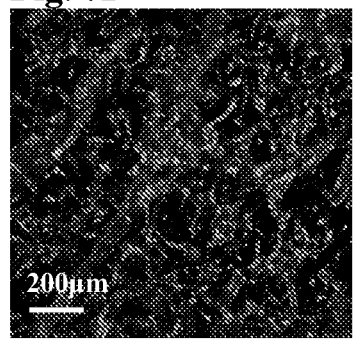
Figure 7C:
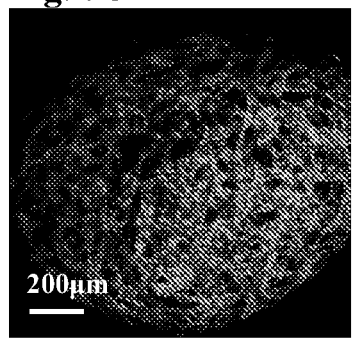
Figure 7G:
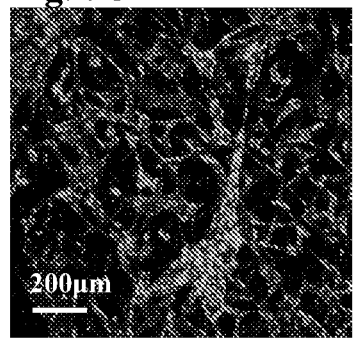
Figure 7D:
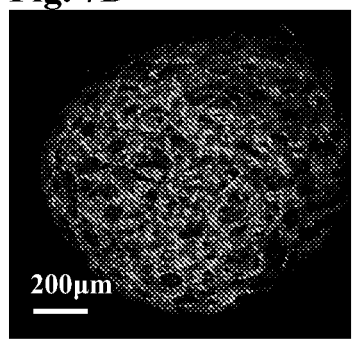
Figure 7H:
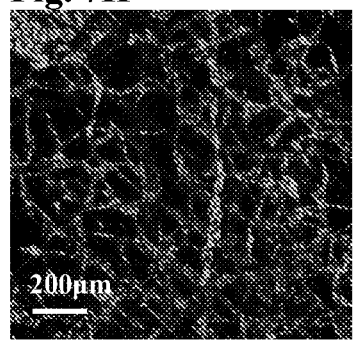
Figure 8A:
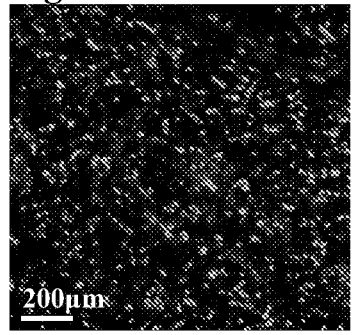
FIGS. 8A-8H show images of HUVEC-GFP labeled sells (8A-8D) and schematic presentations (8E-8H) showing four network patterns: individual cells (8A and 8E), groups of cells which are not connected (8B and 8F), a partially connected network (8C and 8G), and a fully connected network (8D and 8H).
Figure 8E:
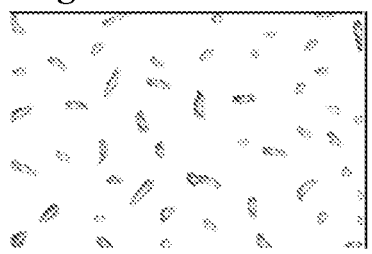
Figure 8B:
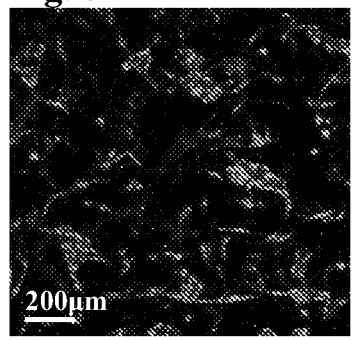
Figure 8F:
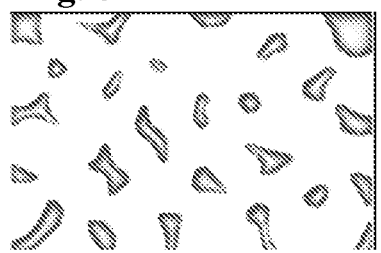
Figure 8C:
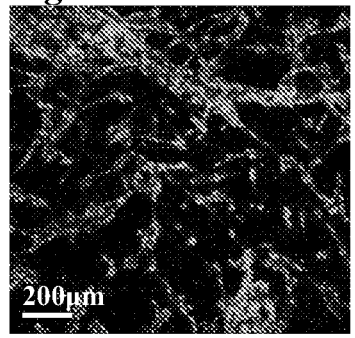
Figure 8G:
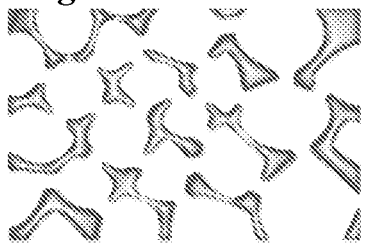
Figure 8D:
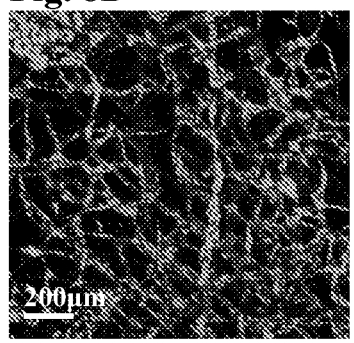
Figure 8H:
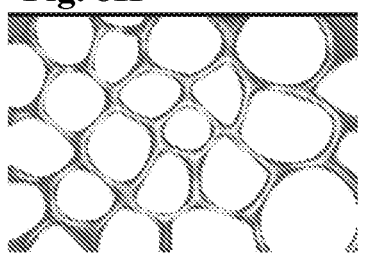

Fibrin-PLLA/PLGA and fibrin-VICRYL™ constructs were prepared as described in Example 2 above. Histological hematoxylin and eosin (H&E) sections show PLLA/PLGA scaffold substances and traces of fibrin matrix (FIG. 5B, pink layer indicated by arrows). Our results show that for higher fibrinogen concentrations the degradation of the fibrin was slower, and higher amounts of fibrin matrix were present throughout the PLLA/PLGA scaffold (FIGS. 5A-5B). For fibrinogen concentration=1 mg/ml, fibrin could not be observed (full degradation). As the fibrinogen concentration was elevated, fibrin was evident to higher extent.

When fibrin was seeded with the co/tri culture cellular preparations and the construct was allowed to float in the medium, its size shrank over time due to forces generated by cells. The percent of shrinkage of fibrin gels was dependent upon fibrinogen concentration used with values of 96±0.7%, 93±0.01%, and 81±3% (co-cultures) and 95±0.5%, 93±0.5%, and 90±1% (tri-cultures) for the 5, 15, and 50 mg/ml fibrinogen concentration, respectively. For instance, in the 5 mg/ml fibrinogen concentration the largest change in construct size was observed (from initial diameter of 6 mm to around 1 mm after 7 days in culture). Importantly, when the PLLA/PLGA synthetic scaffold was added to fibrin gels, construct size remain constant for the entire culture time for all fibrinogen concentrations tested.

Images of 3D fibrin-VICRYL™ construct embedded with co-culture of endothelial and fibroblast cells show that the endothelial cells formed a confluent layer (FIGS. 6D and 6E).

Example 5

Vessel Network Formation Within 3D Fibrin-Based Constructs

In order to obtain insights on vessel network formation during culture time, confocal microscopy allowing capturing large field of view (about 90% of construct area was imaged) was used to follow HUVEC-expressing GFP cells. Fibrin (60 µl) and fibrin (20/60 µl)+PLLA/PLGA constructs embedded with co- or tri-culture preparations (also termed herein after co- or tri-cultures) were monitored following 1, 3, 5, 7 days from cell seeding. After 1 day in culture, the HUVEC-GFP cells were mostly rounded or part of them started to develop elongated morphology, but after 3 days, cellular organization was initiated (FIGS. 7A-7H). Quantification results of vessel network levels during culture time revealed that fibrinogen concentrations and quantities highly influenced the process of network formation (FIGS. 9A-9B). FIGS. 8E-8H show a schematic presentation of the four pattern levels that were classified to semi-quantified network formation. Real images of HUVEC-GFP cells demonstrating the four network patterns are shown in FIGS. 8A-8D. Each network level is represented by blue color nuance, and the greater the intensity of the color, the vessel network is more developed (FIGS. 9A-9B).

Figure 10A:
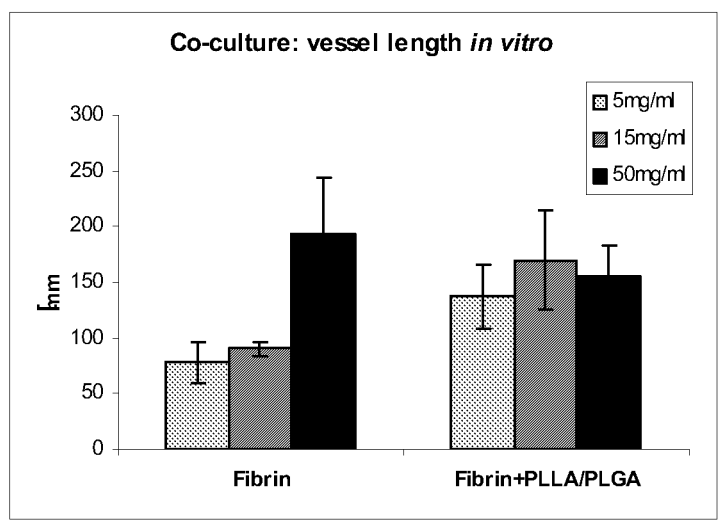
FIGS. 10A-10D show quantification of vessel length (10A and 10C) and vessel thickness (10B and 10D) in vitro, for fibrin or fibrin+PLLA/PLGA constructs embedded with either a co-culture of endothelial and fibroblasts cells (10A-10B) or a tri-culture containing endothelial, myoblasts and fibroblast cells (10C-10D).
Figure 10B:
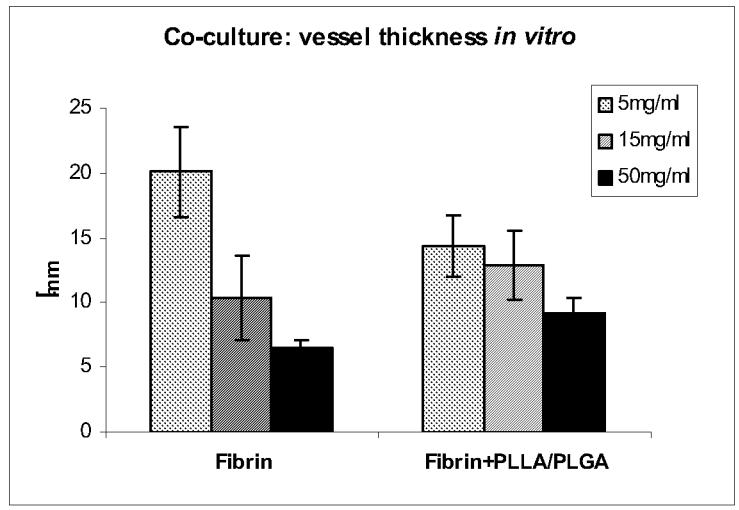

For the co-culture preparations (FIG. 9A), fibrin constructs although shrank dramatically during time, showed gradually increasing level of vessel organization toward connected vessel network at day 7. Fibrin+PLLA/PLGA constructs maintained constant size for the entire culture time allowing gradually increasing levels of openly distributed vessel networks when compared to fibrin constructs (FIGS. 7A-7H). For the fibrin+PLLA/PLGA constructs, the amount of 60 µl fibrin was preferable for vessel network formation for all fibrinogen concentrations tested (FIGS. 9A-9B). After 7 days in culture, for both fibrin and fibrin+ PLLA/PLGA (60 µl) constructs, a tendency toward longer and thinner vessels for elevated fibrinogen concentrations was detected (FIGS. 10A-10B).

Figure 10C:
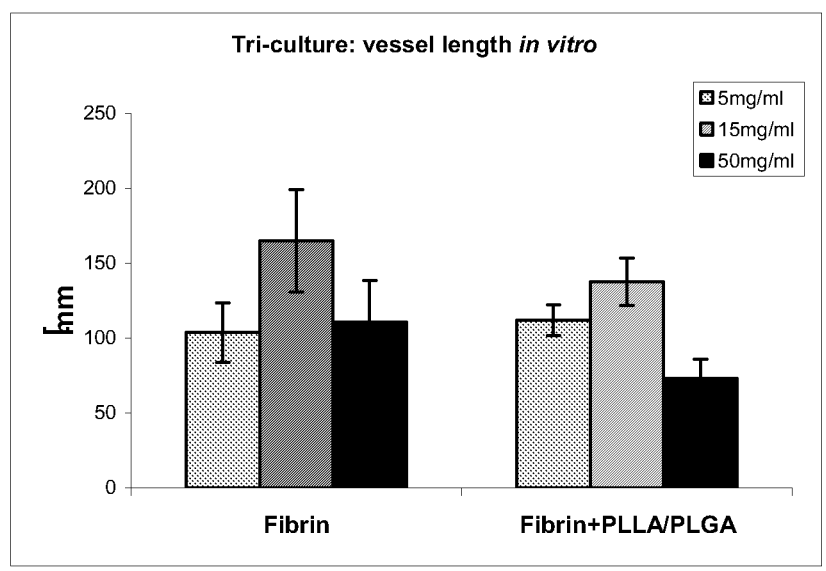
Figure 10D:
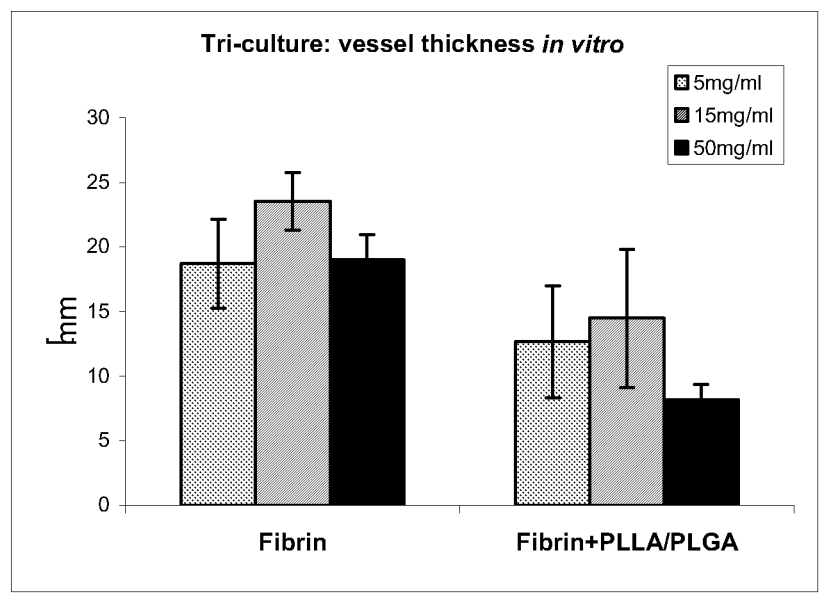

For the tri-culture preparations, vessel network levels were lower when compared to the co-culture preparations (note the decrease in intensity on the right side of (FIG. 9B). Still, fibrin and fibrin+PLLA/PLGA (60 µl) constructs showed gradually increasing level of vessel organization during time in culture. In the fibrin+PLLA/PLGA constructs, the amount of 60 µl fibrin was superior for vessel network formation. After 7 days in culture, an optimal fibrinogen concentration of 15 mg/ml was detected resulting in long and thick vessels (FIGS. 10C-10D).

Importantly, the highest level of vessel network levels, for the co- and tri-culture preparations, was found in the fibrin+ PLLA/PLGA constructs picked at 15 mg/ml fibrinogen concentration. Furthermore, vascularization levels were found to be augmented when compared to PLLA/PLGA scaffold embedded with Matrigel (a common matrix used in 3D culture assays) for the co- and tri-cultures. Based on these results, precursor fibrinogen concentration of 15 mg/ml was selected for the in vivo implantation studies.

Example 6

Differentiation of Fibroblasts and Myoblasts in Vitro

A critical step toward formation of stabilized and mature vessel network is the incorporation of mural cells (smooth muscle/pericytes cells) into the primitive endothelial vessels. To analyze whether the fibroblast cells differentiated into smooth muscle-like cells within the fibrin-based constructs (fibrin and fibrin+PLLA/PLGA constructs), whole constructs or cross-sections were immunofluorescently stained with antibodies against alpha smooth muscle actin (αSMA). FIGS. 11A-11D show confocal image projections of whole constructs embedded with HUVEC-GFP and fibroblast cells and immunofluorescently stained following 7 days with αSMA antibody demonstrating the presence of smooth muscle-like cells. Double staining for VWF (endothelial maker) and αSMA on cross-sections revealed the presence of smooth muscle cells and their localization around endothelial lumen vessels (FIGS. 11E-11G, in various magnifications).

Figure 12A:
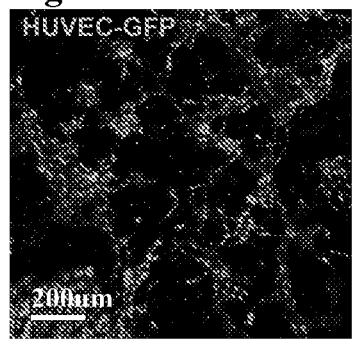
FIGS. 12A-12D show confocal image projections of whole fibrin or fibrin+PLLA/PLGA constructs embedded with a tri-culture of endothelial, myoblast and fibroblast cells, wherein HUVEC cells were labeled with GFP (12A and 12C) and the constructs were immunofluorescently stained with desmin antibody indicating that the myoblast cells continue to form elongated myotubes (12B and 12D).
Figure 12B:
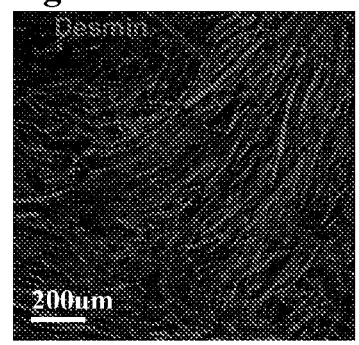
Figure 12C:
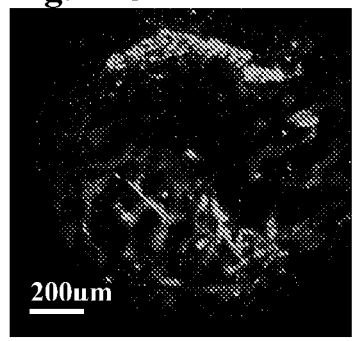
Figure 12D:
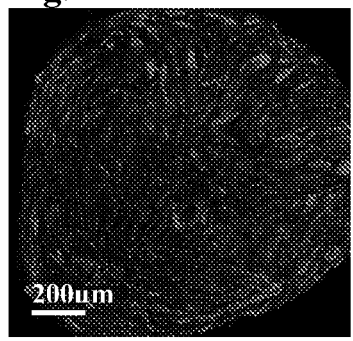

In the tri-culture preparations, the myoblast cells continue to form elongated myotubes as indicated by immunostaining with Desmin antibody (FIGS. 12B and 12D). We did not note any specific impact of fibrinogen concentration on the degree of differentiation toward skeletal myotubes.

Example 7

In Vivo Implantation Studies

Figure 13A:
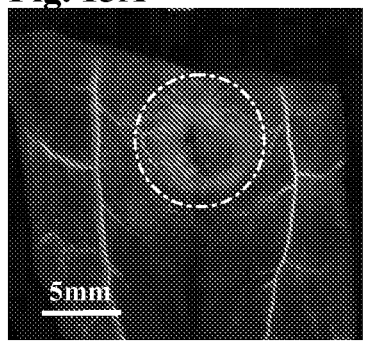
FIGS. 13A-13C show images of constructs of acellular fibrin (13A) or acellular fibrin+PLLA/PLGA (13B and 13C) implanted into the linea-alba of nude mice. Injection of FITC-Dextran to the blood circulation revealed intense host-derived vessels penetrating and perfusing the engrafted area (13A, green signal). Bright field images clearly highlight the graft area, the host neovessels penetrating to the graft area, and the existence of pore structure belonging to the implanted PLLA/PLGA (13C).
Figure 13B:
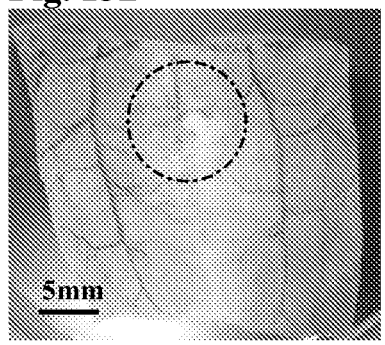
Figure 13C:
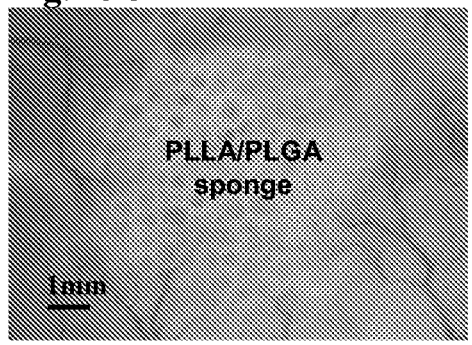
Figure 14A:
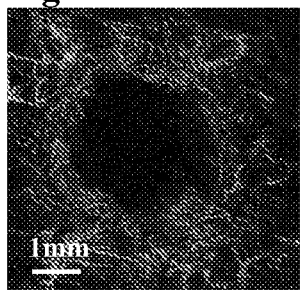
FIGS. 14A-14L show images of constructs of acellular fibrin (14A, 14B and 14C), fibrin embedded with co-culture of HUVEC and fibroblast cells (14D, 14E and 14F), acellular fibrin+PLLA/PLGA (14G, 14H and 14I), and fibrin+PLLA/PLGA embedded with co-culture preparation (14J, 14K and 14L) which were implanted into the linea-alba of nude mice. Injection of FITC-Dextran to the blood circulation revealed intense host-derived vessels penetrating and perfusing the engrafted area (14A, 14D, 14G and 14J, green signal). Histological examination (H&E staining) demonstrated that blood vessels occupied with red blood cells were evident in the graft area (14B, 14C, 14E, 14F, 14H, 14I, 14K and 14L).
Figure 14B:
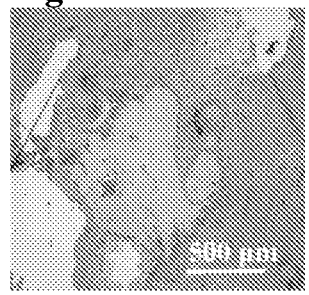
Figure 14C:
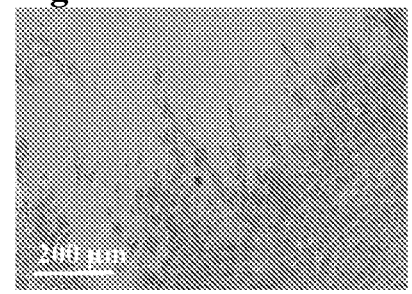
Figure 14D:
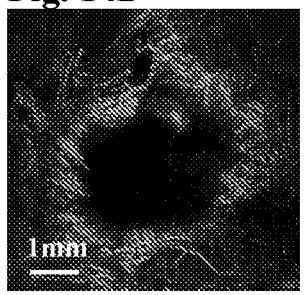
Figure 14E:
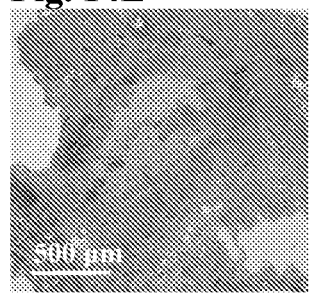
Figure 14F:
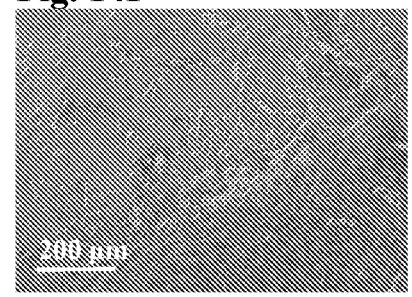
Figure 14G:
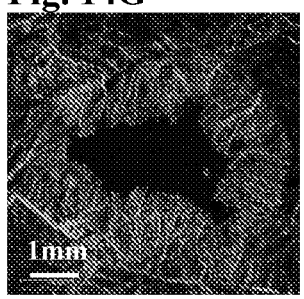
Figure 14H:
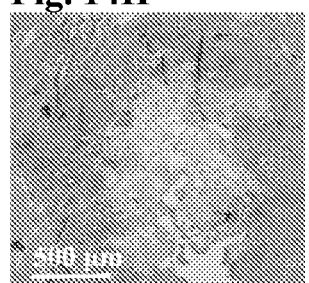
Figure 14I:
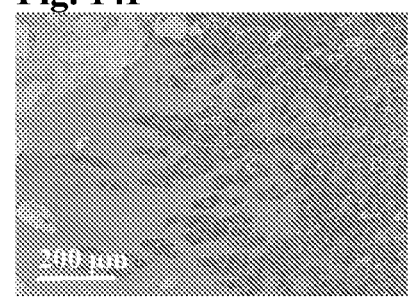
Figure 14J:
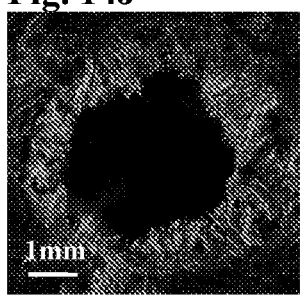
Figure 14K:
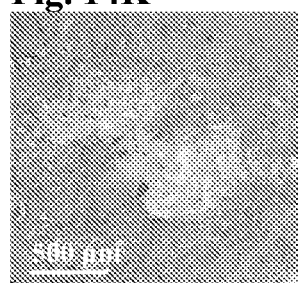
Figure 14L:
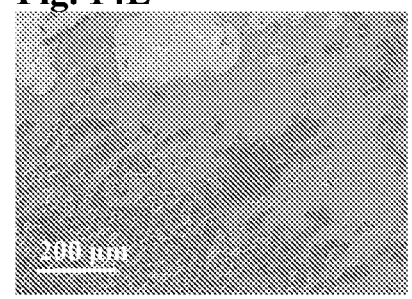
Figure 15A:
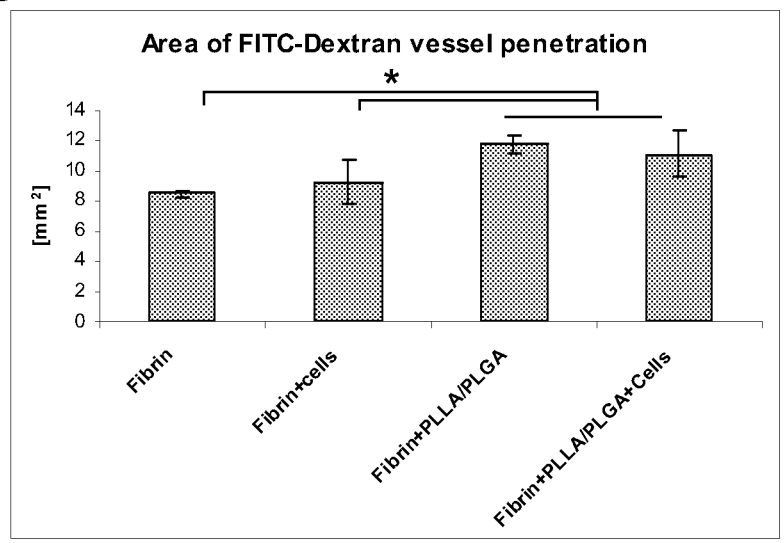
FIGS. 15A-15B show quantification of the area of FITC-Dextran+ blood vessels penetrating the graft (15A) as well as calculation of the graft area size (15B). The results indicate that implantation of fibrin+PLLA/PLGA constructs provided significantly higher area of penetrating FITC-Dextran+ blood vessels (15A) and significantly higher graft size (15B) when compared to fibrin constructs. No significant difference was found between cellular and acellular constructs.
Figure 15B:
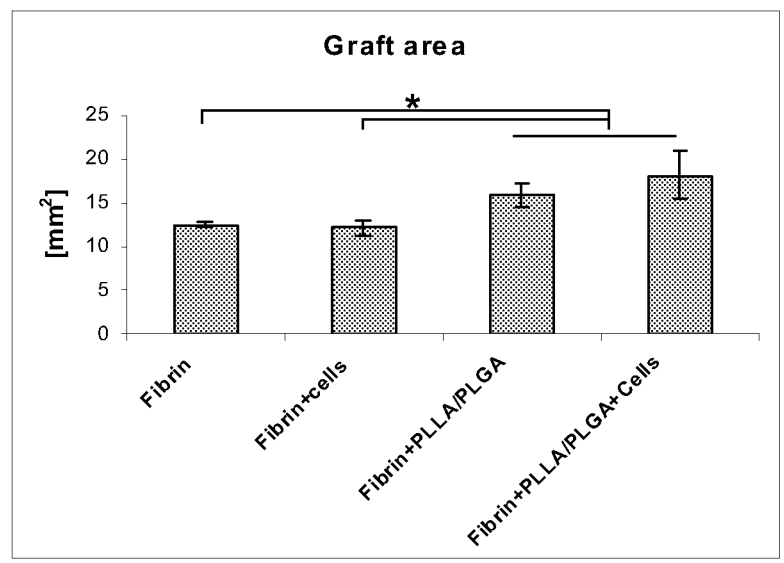

Successful implantation of tissue-engineered construct is largely dependent on host neovascularization and anastomosis of implant with host vasculature. To evaluate the ability of fibrin and fibrin+PLLA/PLGA constructs to promote graft neovascularization and perfusion in vivo, four types of constructs were implanted into the linea-alba of nude mice including: acellular fibrin, fibrin embedded with co-culture preparation, acellular fibrin+PLLA/PLGA, and fibrin+PLLA/PLGA embedded with co-culture preparation (FIGS. 13A-13C and 14A-14L). Based on our in vitro results, we chose to focus on fibrin concentration of 15 mg/ml in the quantity of 60 μl for all implanted constructs. Bright field images clearly highlight the graft area, the host neovessels penetrating to the graft area, and the existence of pore structure belonging to the implanted PLLA/PLGA (FIG. 13C). Injection of FITC-Dextran to the blood circulation revealed intense host-derived vessels penetrating and perfusing the engrafted area (FIGS. 13A, 14A, 14D, 14G and 14J, green signal). Histological examination (H&E staining, FIGS. 14B, 14C, 14E, 14F, 14H, 14I, 14K and 14L) demonstrated that blood vessels occupied with red blood cells were evident in the graft area. Our unique in vivo model enabled calculation of the area of FITC-Dextran+ blood vessels penetrating the graft (FIG. 15A) as well as calculation of the graft area size (FIG. 15B). Results of these measurements revealed that implantation of fibrin+PLLA/PLGA constructs provided significantly higher area of penetrating FITC-Dextran+ blood vessels and significantly higher graft size when compared to fibrin constructs (FIGS. 15A-15B). No significant difference was found between cellular and acellular constructs.

Example 8

Formation of 3D Human Vessel Network in Vivo

Figure 16A:
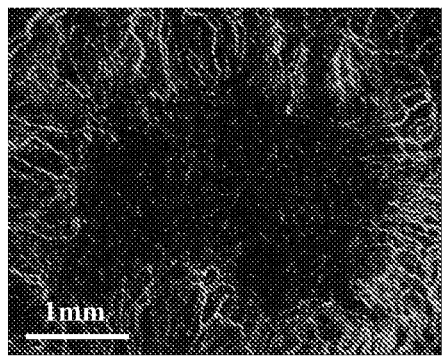
FIGS. 16A-16F show images of constructs of fibrin, fibrin+PLLA/PLGA and PLLA/PLGA embedded with HUVEC cells expressing red fluorescence protein (RFP, red signal) which were implanted into the linea-alba of nude mice Injection of FITC-Dextran to the blood circulation revealed intense host-derived vessels penetrating and perfusing the engrafted area (green signal). HUVEC-RFP cells implanted within the fibrin+PLLA/PLGA constructs formed 3D inter-connected array of vessel network in vivo (16C). The vessels had large vacuoles in the tubes (16C, arrows) which resembled those of native blood vessels. Careful examination of the implant-host integration area demonstrated close interactions between tubes formed by implanted endothelial cells and host neovessels penetrating the graft area, as well as the presence of mosaic implant/host vessels (16D-16F).
Figure 16B:
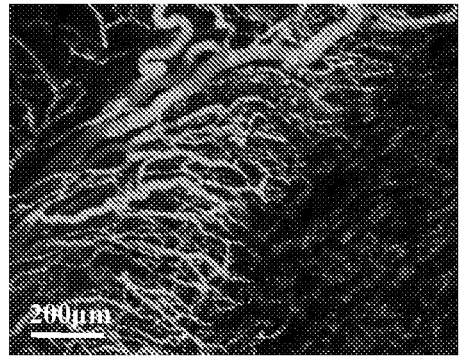
Figure 16C:
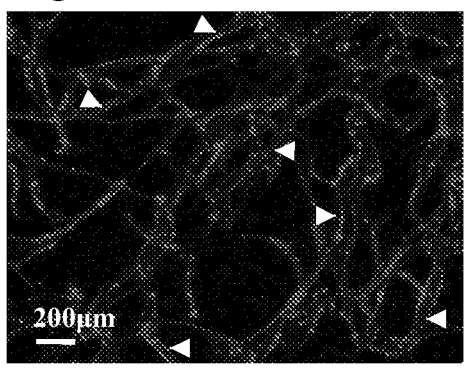
Figure 16D:
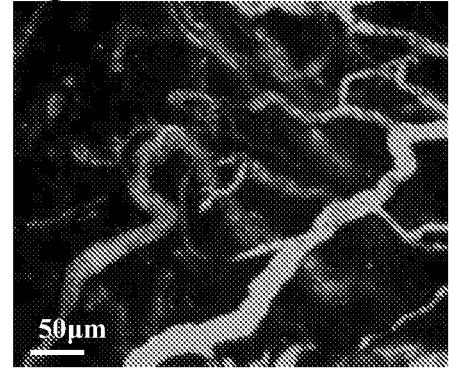
Figure 16E:
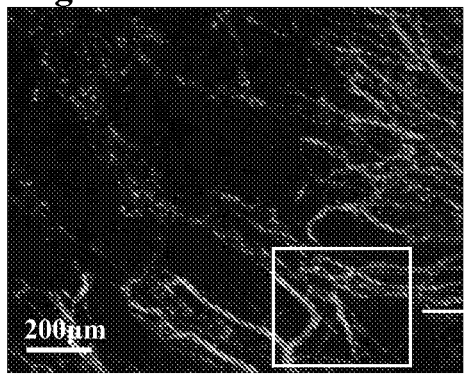
Figure 16F:
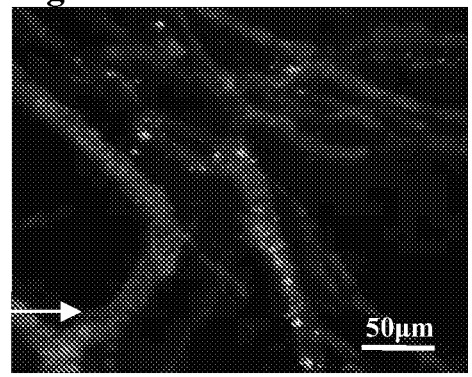
Figure 17A:
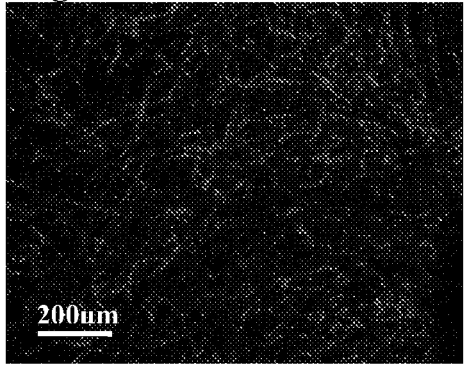
FIGS. 17A-17F show images of constructs of fibrin, fibrin+PLLA/PLGA and PLLA/PLGA embedded with HUVEC-RFP labeled cells (17A, 17B and 17C, respectively) and image computer analysis of these images (17D-17F) determining total network length and area in vivo.
Figure 17D:
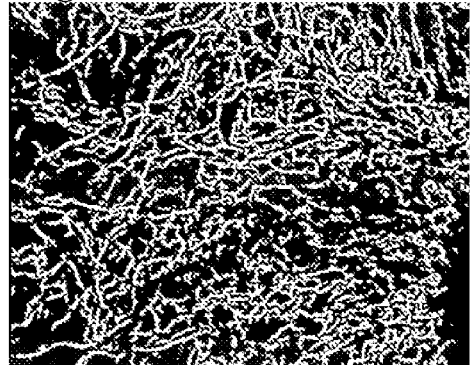
Figure 17B:
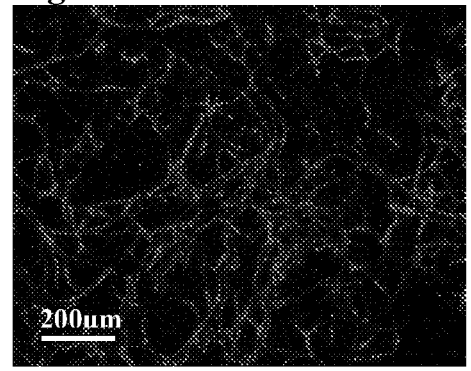
Figure 17E:
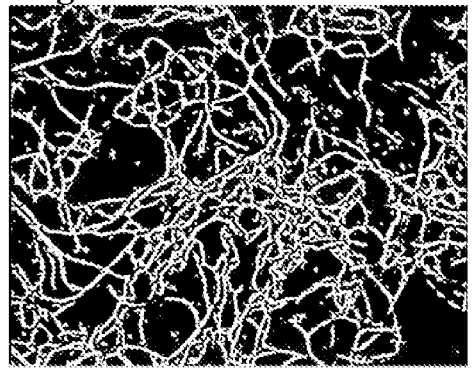
Figure 17C:
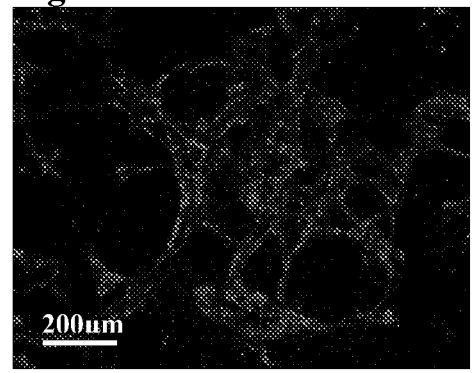
Figure 17F:
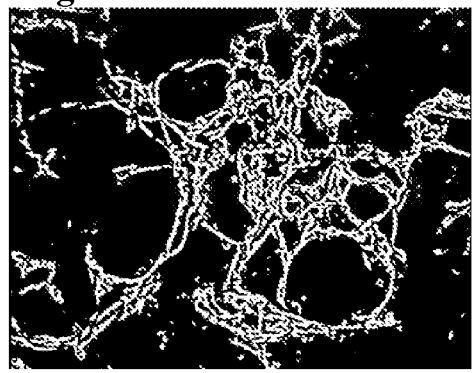
Figure 18A:
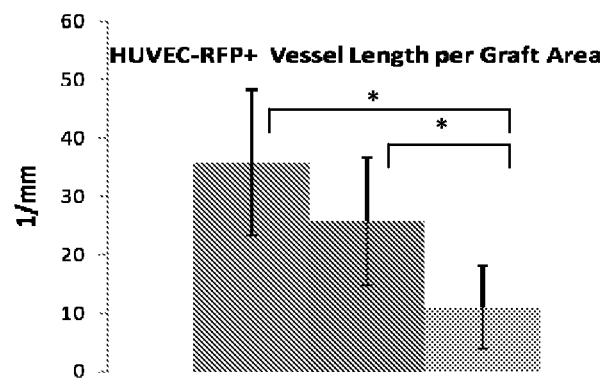
FIGS. 18A-18B show quantitative analysis of total vessel network length (18A) and area (18B) in vivo. The network architectures and density differed in the three constructs. The total area and length density was augmented in the fibrin and fibrin+PLLA/PLGA constructs when compared to PLLA/PLGA construct without fibrin (18A-18B). No statistical difference was observed between fibrin and fibrin+PLLA/PLGA constructs (18A-18B).
Figure 18B:
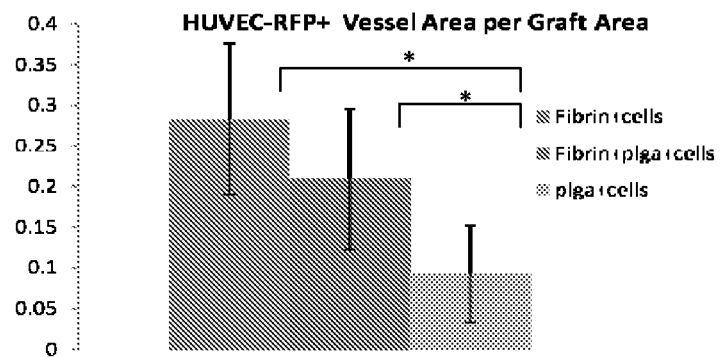
Figure 19A:
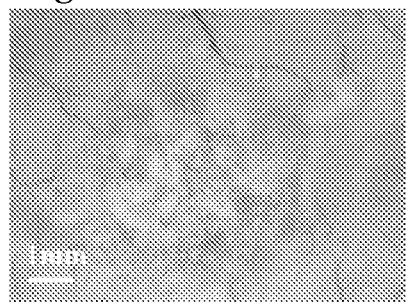
FIGS. 19A-19G show images of constructs of fibrin+PLLA/PLGA embedded with HUVEC cells expressing red fluorescence protein (RFP, red signal) which were implanted into the linea-alba of nude mice: 19A and 19D bright field images, 19B and 19E fluorescence image of FITC-Dextran injected to the blood circulation, 19C and 19F fluorescence image of HUVEC-RFP cells and 19G is a combination of FITC-Dextran and HUVEC-RFP. Bright field images clearly captured HUVEC-RFP vessels located in the graft area, which contained red blood cells supporting their functional perfusion capabilities.
Figure 19D:
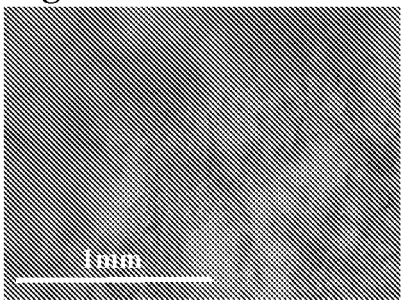
Figure 19B:
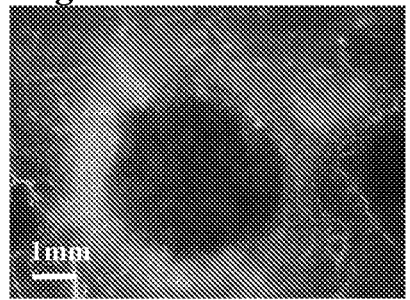
Figure 19E:
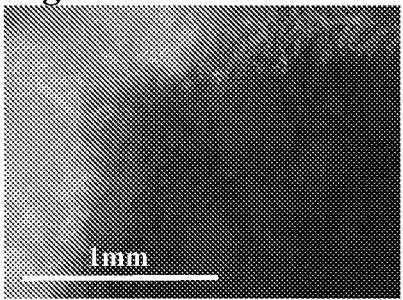
Figure 19C:
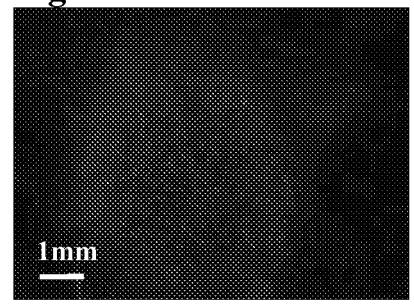
Figure 19F:
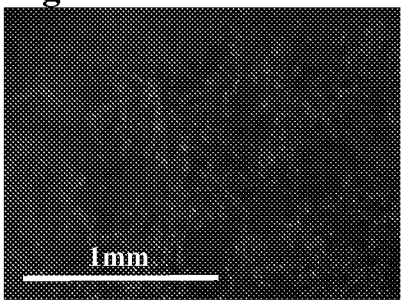
Figure 19G:
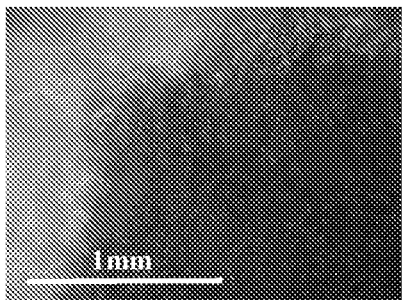

An important aspect of the present experiments was to explore the fate of the implanted human endothelial cells, and to determine whether they managed to organize into 3D inter-connected vessel network in vivo as was observed in vitro. Also, the query of host and implanted-HUVEC vessels integration was investigated. For that reason, HUVEC-expressing RFP (red signal) were used in all implantation experiments allowing to identify them in vivo and at the same time visualizing FITC-Dextran functional vessels (green signal) (FIGS. 16A-16B). Using our unique in vivo model along with advanced confocal high field imaging, we successfully captured construct vascular trees in vivo and followed the fate of implanted HUVEC-RFP cells in three different implanted constructs: fibrin, fibrin+PLLA/PLGA, and PLLA/PLGA. The PLLA/PLGA scaffold was now added in order to analyze the impact of fibrin on cell retention in vivo. Our results indicate that HUVEC-RFP cells implanted within the fibrin and fibrin+PLLA/PLGA constructs formed 3D inter-connected array of vessel network in vivo (FIG. 16C). The vessels had large vacuoles in the tubes (FIG. 16C, arrows) which resembled those of native blood vessels. Careful examination of the implant-host integration area demonstrated close interactions between tubes formed by implanted endothelial cells and host neovessels penetrating the graft area, as well as the presence of mosaic implant/host vessels (FIGS. 16D-16F). Quantitative analysis of HUVEC-RFP cells was performed using automated image analysis algorithms determining total network length and area in vivo (FIGS. 17D-17F). The network architectures and density differed in the three constructs as highlighted in FIGS. 17D-17F. The total area (FIG. 18B) and length (FIG. 18A) was augmented in the fibrin and fibrin+PLLA/PLGA constructs when compared to PLLA/PLGA construct without fibrin. No statistical difference was observed between fibrin and fibrin+PLLA/PLGA constructs (FIGS. 18A-18B). Although host and implanted vessels were shown to be in close proximity, and to form mosaic implant/host vessels, FITC-Dextran was not evident within HUVEC-RFP lined vessels. Nevertheless, bright field images clearly captured HUVEC-RFP vessels located in the graft area which contained red blood cells supporting their functional perfusion capabilities (FIGS. 19A and 19D).

Additionally, the total amount of human cellular DNA extracted from the implanted constructs was evaluated using real-time PCR analysis employing the human specific RNAse P gene. The single copy human RNAse P gene was previously reported to be suitable for human cells quantification. Hence, the total human cellular DNA was found to be similar in the fibrin and fibrin+PLLA/PLGA constructs providing PCR cycle averages (absolute analysis) of 32.2±1 and 32.8±2 respectively when compared to 36.5±1 for the PLLA/PLGA construct.

REFERENCES

Caspi O, Lesman A, Basevitch Y, Gepstein A, Arbel G, Habib I H, Gepstein L, Levenberg S. (2007) Tissue engineering of vascularized cardiac muscle from human embryonic stem cells. Circ Res. 100(2):263-72.

Holder W D Jr, Gruber H E, Moore A L, Culberson C R, Anderson W, Burg K J, Mooney D J. (1998) Cellular ingrowth and thickness changes in poly-L-lactide and polyglycolide matrices implanted subcutaneously in the rat. J Biomed Mater Res. 41(3):412-21.

Langer R, Vacanti J P. (1993) Tissue engineering. Science. 260(5110):920-6.

Lesman A, Habib M, Caspi O, Gepstein A, Arbel G, Levenberg S, Gepstein L. (2010) Transplantation of a tissue-engineered human vascularized cardiac muscle. Tissue Eng Part A. 16(1):115-25.

Levenberg S, Rouwkema J, Macdonald M, Garfein E S, Kohane D S, Darland D C, Marini R, van Blitterswijk C A, Mulligan R C, D'Amore P A, Langer R. (2005) Engineering vascularized skeletal muscle tissue. Nat Biotechnol. 23(7):879-84. Epub 2005 Jun. 19.

Mooney D J, Sano K, Kaufmann P M, Majahod K, Schloo B, Vacanti J P, Langer R. (1997) Long-term engraftment of hepatocytes transplanted on biodegradable polymer sponges. J Biomed Mater Res. 37(3):413-20.

Victor W. M. Van hinsbergh, Annemie Collen, and Pieter Koolwijk. (2001) Role of Fibrin Matrix in Angiogenesis. Ann N Y Acad Sci. 936:426-37.

Chen X, Aledia A S, Ghajar C M, Griffith C K, Putnam A J, Hughes C C W, and George S C (2009) Prevascularization of a Fibrin-Based Tissue Construct Accelerates the Formation of Functional Anastomosis with Host Vasculature. Tissue Eng part A. 15(6):1363-1371.

Montano I R, Schiestl C, Schneider J, Pontiggia L, Luginbuhl L, Biedermann T, Bottcher-Haberzeth S, Braziulis E, Meuli M, and Reichmann E (2010) Formation of Human Capillaries In Vitro: The Engineering of Prevascularized Matrices. Tissue Eng part A. 16(1): 269-282.

Vailhe B, Ronot X, Tracqui P, Usson Y, and Tranqui L (1997) In vitro angiogenesis is modulated by the mechanical properties of fibrin gels and is related to $\alpha_v\beta_3$ integrin localization. In vitro Cell. Dev. Biol. Animal 33:763-773.

The invention claimed is:

1. A three-dimensional hybrid tissue engineering construct comprising a porous polymeric synthetic scaffold, said scaffold carrying throughout the pores thereof fibrin gel having therein an interconnected vascular network of blood vessels, with the proviso that the construct contains no soluble basement membrane matrix extracted from Engelbreth-Holm-Swarm mouse tumor cells.

2. The three-dimensional hybrid tissue engineering construct according to claim 1, wherein said fibrin gel is prepared from fibrinogen having a concentration of at least 7 mg/ml.

3. The three-dimensional hybrid tissue engineering construct according to claim 2, comprising endothelial cells, fibroblasts, and muscle cells, and wherein the polymeric synthetic scaffold is a PLLA/PLGA sponge.

4. The three-dimensional hybrid tissue engineering construct according to claim 3, wherein the ratio of endothelial cells and fibroblasts is between 1:2 and 1:10, and the ratio between endothelial cells and muscle cells is about 1:1.

5. The three-dimensional hybrid tissue engineering construct according to claim 1, wherein said fibrinogen concentration is 15 mg/ml.

6. A pharmaceutical composition comprising the three-dimensional hybrid tissue engineering construct according to claim 1, and a physiologically acceptable carrier.

7. The pharmaceutical composition according to claim 6, wherein the three-dimensional hybrid tissue engineering construct comprises tissue-specific cells.

8. The pharmaceutical composition according to claim 7, wherein said tissue-specific cells are muscle cells.

9. The three-dimensional hybrid tissue engineering construct according to claim 1, wherein said porous polymeric synthetic scaffold is made of a material selected from the group consisting of a combination of PLLA (poly-l-lactic acid) and PLGA (polylactic-co-glycolic acid) (PLLA/PLGA), polyglycolic acid (PGA), polylactic acid (PLA), PLA-PGA co-polymer, poly(glycerol sebacate) (PGS), poly (anhydride), poly(hydroxy acid), poly(ortho ester), poly (propylfumerate), poly(caprolactone), polyamide, polyamino acid, polyacetal, biodegradable polycyanoacrylate, biodegradable polyurethane and polysaccharide, polypyrrole, polyaniline, polythiophene, polystyrene, polyester, non-biodegradable polyurethane, polyurea, poly(ethylene vinyl acetate), polypropylene, polymethacrylate, polyethylene, polycarbonate and poly(ethylene oxide).

10. The three-dimensional hybrid tissue engineering construct according to claim 9, wherein said porous polymeric synthetic scaffold is a sponge comprising a 50:50 mixture of PLLA/PLGA or a mesh comprising polyglycolic acid.

11. The three-dimensional hybrid tissue engineering construct according to claim 1, wherein said porous polymeric synthetic scaffold is not in the form of a mesh.

12. The three-dimensional hybrid tissue engineering construct according to claim 1, wherein said porous polymeric synthetic scaffold has a pore size of 600 µm or less.

13. The three-dimensional hybrid tissue engineering construct according to claim 1, wherein said interconnected vascular network of blood vessels comprises endothelial cells, fibroblasts and, optionally, tissue specific cells.

14. The three-dimensional hybrid tissue engineering construct according to claim 13, wherein the fibroblast cells are human foreskin fibroblasts.

15. The three-dimensional hybrid tissue engineering construct according to claim 13, wherein the endothelial cells are selected from the group consisting of adult vein endothelial cells, adult artery endothelial cells, embryonic stem cell-derived endothelial cells, iPS-derived endothelial cells, umbilical vein endothelial cells, umbilical artery endothelial cells, endothelial progenitor cells derived from bone marrow, endothelial progenitor cells derived from cord blood, endothelial progenitor cells derived from peripheral blood, and endothelial progenitor cells derived from adipose tissues.

16. The three-dimensional hybrid tissue engineering construct according to claim 15, wherein the endothelial cells are human umbilical vein endothelial cells (HUVEC).

17. The three-dimensional hybrid tissue engineering construct according to claim 13, wherein the fibroblast cells are selected from the group consisting of-human embryonic fibroblasts, mouse embryonic fibroblasts, skin fibroblast cells, vascular fibroblast cells, myofibroblasts, and mesenchymal stem cells (MSCs)-derived fibroblast cells.

18. The three-dimensional hybrid tissue engineering construct according to claim 13, comprising endothelial cells, fibroblasts and tissue-specific cells, wherein the tissue-specific cells are selected from the group consisting of muscle cells, pancreatic beta cells, osteoblasts, chondrocytes, adipocytes, neuronal cells, glial cells, cardiomyocytes, liver cells, urethral cells, kidney cells, periosteal cells, bladder cells, dental pulp cells, periodontal cells, tenocytes, lung cells, cardiac cells, skeletal cells, smooth muscle cells, stem cell, iPS cell derived tissue-specific cells, and a combination thereof.

19. The three-dimensional hybrid tissue engineering construct according to claim 13, comprising endothelial cells, fibroblasts and tissue-specific cells, wherein the tissue-specific cells are selected from the group consisting of myoblasts, pancreatic beta-islet cells, cardiomyocytes, liver cells, lung cells, neural cells, bone and kidney cells.

20. The three-dimensional hybrid tissue engineering construct according to claim 13, comprising HUVEC and human foreskin fibroblast cells or HUVEC, human foreskin fibroblast cells and myoblasts, encapsulated within a hybrid scaffold of fibrin gel and a polymeric synthetic scaffold selected from the group consisting of a PLLA/PLGA sponge and a polyglycolic acid mesh.

21. A three-dimensional hybrid tissue engineering construct in accordance with claim 1, made by a process comprising:
   (i) mixing endothelial cells, fibroblasts and, optionally, tissue specific cells with thrombin and with fibrinogen to form a mixture and causing said mixture to enter the pores of said porous polymeric synthetic scaffold;
   (ii) incubating the scaffold to allow the thrombin and fibrinogen to polymerize and form a porous scaffold with fibrin gel mixed with said cells being present throughout the porous scaffold; and
   (iii) growing the porous scaffold formed after said polymerization step under conditions sufficient to permit formation of an interconnected vascular network of blood vessels within the construct.

22. The three-dimensional hybrid tissue engineering construct in accordance with claim 21, wherein step (i) comprises the following steps:
   mixing endothelial cells, fibroblasts and, optionally, tissue specific cells with thrombin to form a mixture and causing said mixture to enter the pores of said porous polymeric synthetic scaffold; and
   adding fibrinogen to the mixture of thrombin and cells in the porous polymeric synthetic scaffold and causing the fibrinogen to enter the scaffold pores.

* * * * *